US008551173B2

(12) United States Patent
Lechmann et al.

(10) Patent No.: US 8,551,173 B2
(45) Date of Patent: Oct. 8, 2013

(54) EXPANDABLE INTERVERTEBRAL IMPLANT AND ASSOCIATED METHOD OF MANUFACTURING THE SAME

(75) Inventors: Beat Lechmann, Grenchen (CH); Dominique Burkard, Grezenbach (CH); Johann Fierlbeck, Salzburg (AT); Alfred Niederberger, Salzburg (AT)

(73) Assignee: DePuy Synthes Products, LLC, Raynham, MA (US)

( * ) Notice: Subject to any disclaimer, the term of this patent is extended or adjusted under 35 U.S.C. 154(b) by 421 days.

(21) Appl. No.: 12/812,146

(22) PCT Filed: Jan. 21, 2009

(86) PCT No.: PCT/US2009/031567
§ 371 (c)(1),
(2), (4) Date: Jul. 8, 2010

(87) PCT Pub. No.: WO2009/092102
PCT Pub. Date: Jul. 23, 2009

(65) Prior Publication Data
US 2010/0286783 A1    Nov. 11, 2010

Related U.S. Application Data

(60) Provisional application No. 61/021,778, filed on Jan. 17, 2008.

(51) Int. Cl.
*A61F 2/44* (2006.01)
*B05D 3/00* (2006.01)
*B05D 3/06* (2006.01)

(52) U.S. Cl.
USPC ..................................... 623/17.12

(58) Field of Classification Search
USPC ............... 606/60, 246–279; 623/17.11–17.16
See application file for complete search history.

(56) References Cited

U.S. PATENT DOCUMENTS

| | | | |
|---|---|---|---|
| 2003/0023305 A1* | 1/2003 | McKay | |
| 2003/0078667 A1* | 4/2003 | Manasas et al. | 623/17.15 |
| 2004/0186577 A1 | 9/2004 | Ferree | |
| 2005/0261769 A1* | 11/2005 | Moskowitz et al. | 623/17.11 |
| 2008/0021556 A1* | 1/2008 | Edie | 623/17.11 |
| 2010/0286783 A1 | 11/2010 | Lechmann et al. | |

FOREIGN PATENT DOCUMENTS

| | | |
|---|---|---|
| CN | 101909548 A | 12/2010 |
| EP | 1683593 | 7/2006 |
| JP | 2011-509766 A | 3/2011 |
| WO | WO 2005/112834 | 12/2005 |
| WO | WO 2009/092102 | 7/2009 |

* cited by examiner

*Primary Examiner* — Kevin T Truong
*Assistant Examiner* — Christopher Beccia
(74) *Attorney, Agent, or Firm* — Woodcock Washburn LLP

(57) ABSTRACT

An expandable intervertebral implant (10) includes superior (20) and inferior (30) bone contacting members and at least one vertical wire netting (50) interconnecting the superior and inferior bone contacting members. The superior and inferior bone contacting members include at least two bone contacting components interconnected via one or more lateral wire nettings such that the implant is vertically and laterally expandable in situ from a first insertion configuration to a second expanded configuration. The vertical and lateral wire netting are preferably constructed of a plurality of individual link members. The present invention also preferably relates to an associated method of manufacturing the intervertebral implant such that the intervertebral implant can be manufactured as an integral component or part.

31 Claims, 19 Drawing Sheets

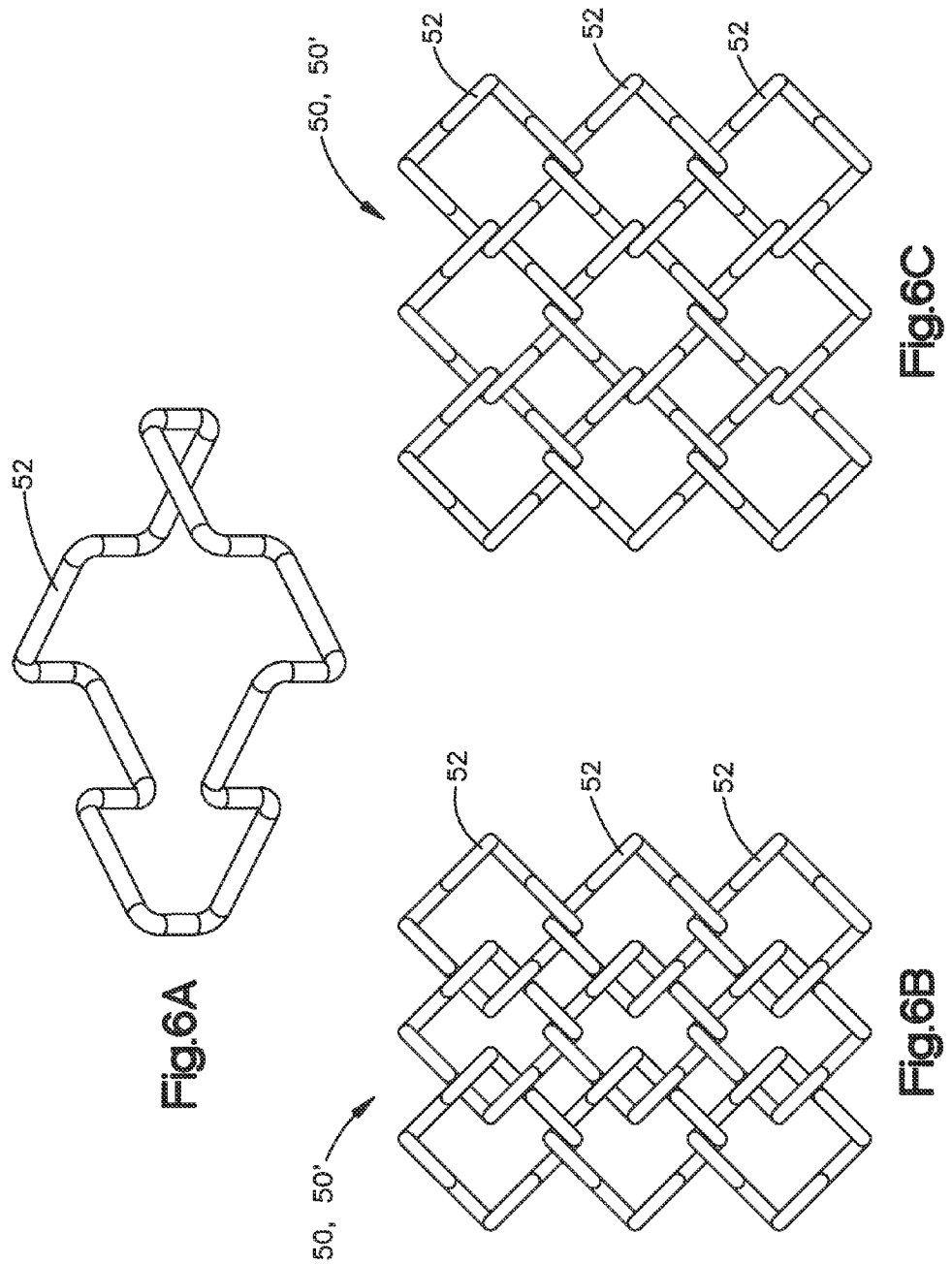

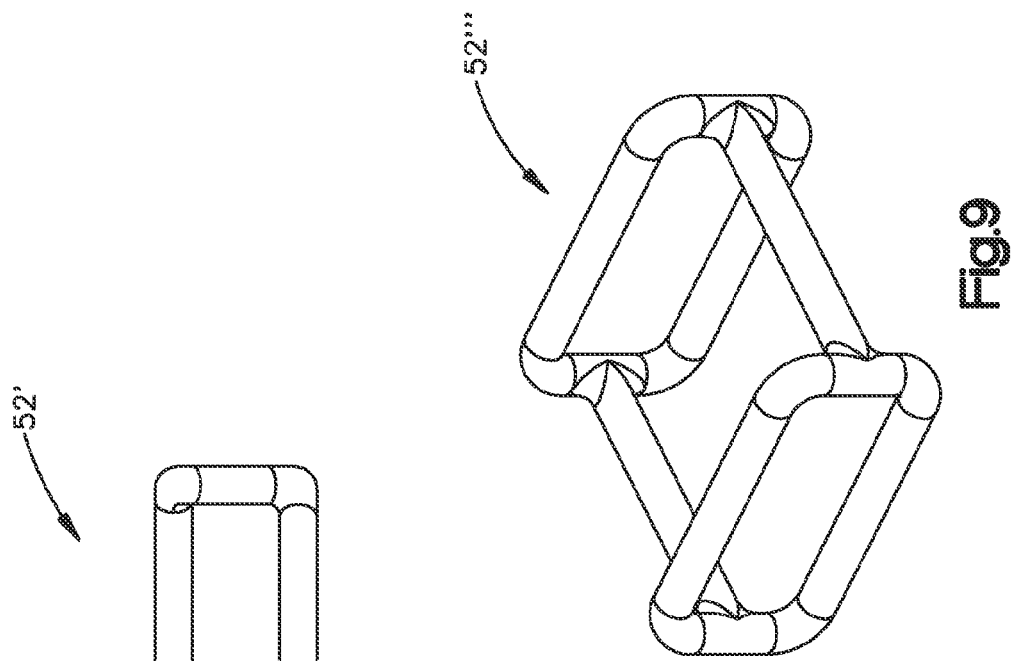
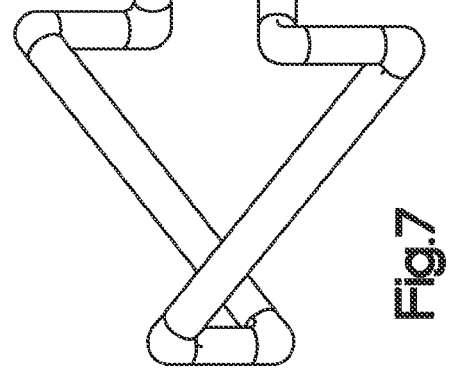
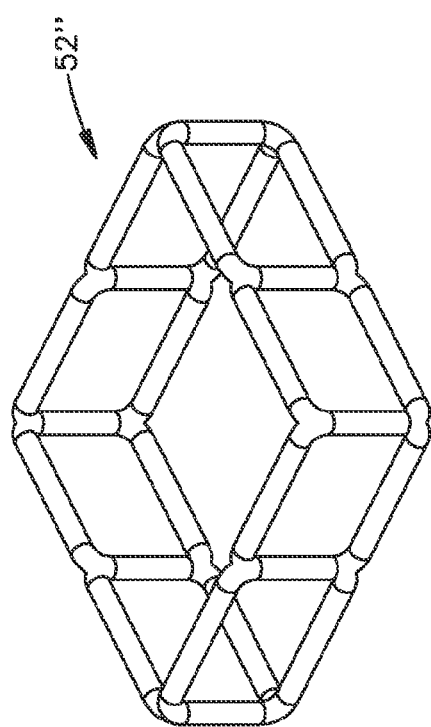

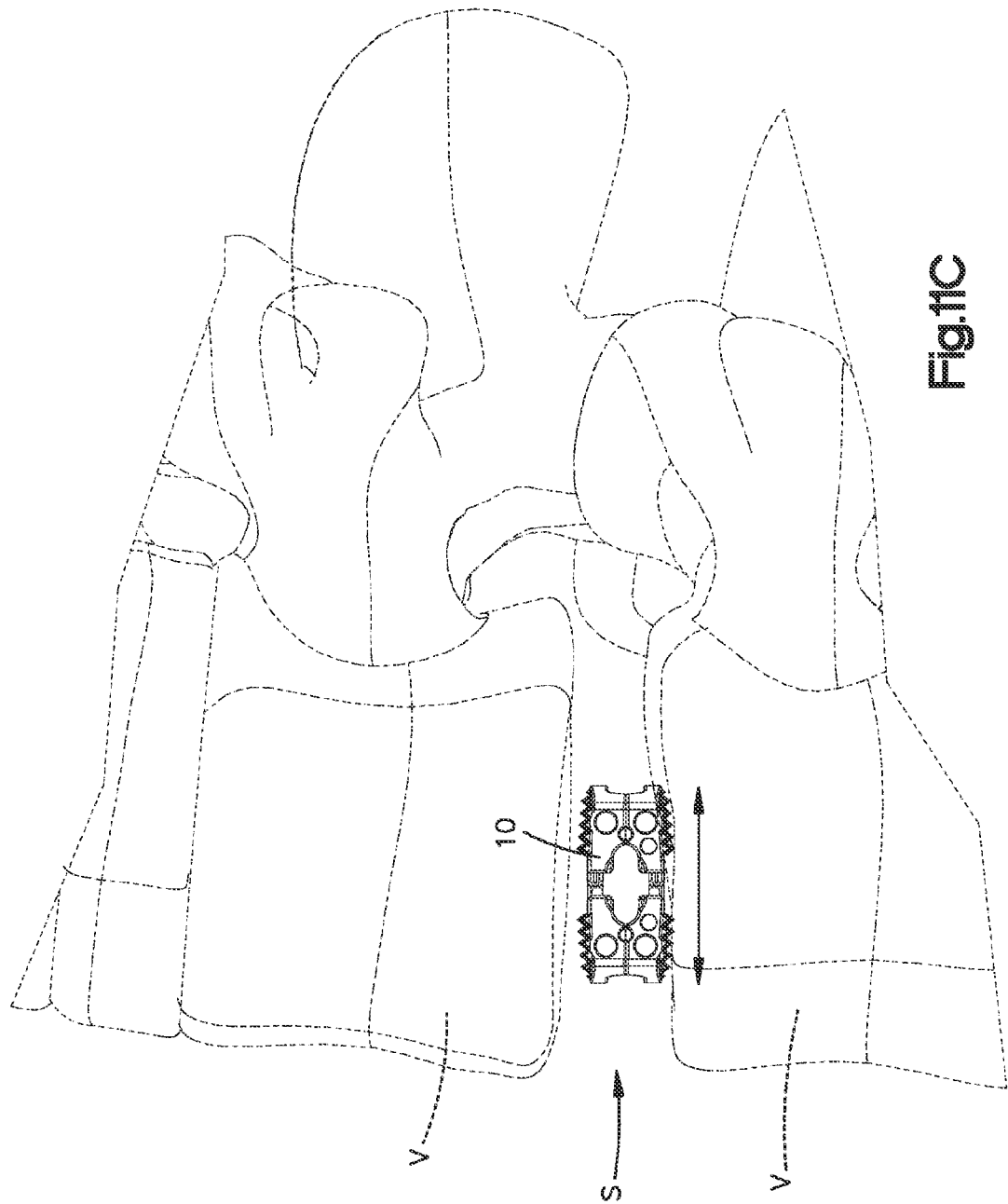

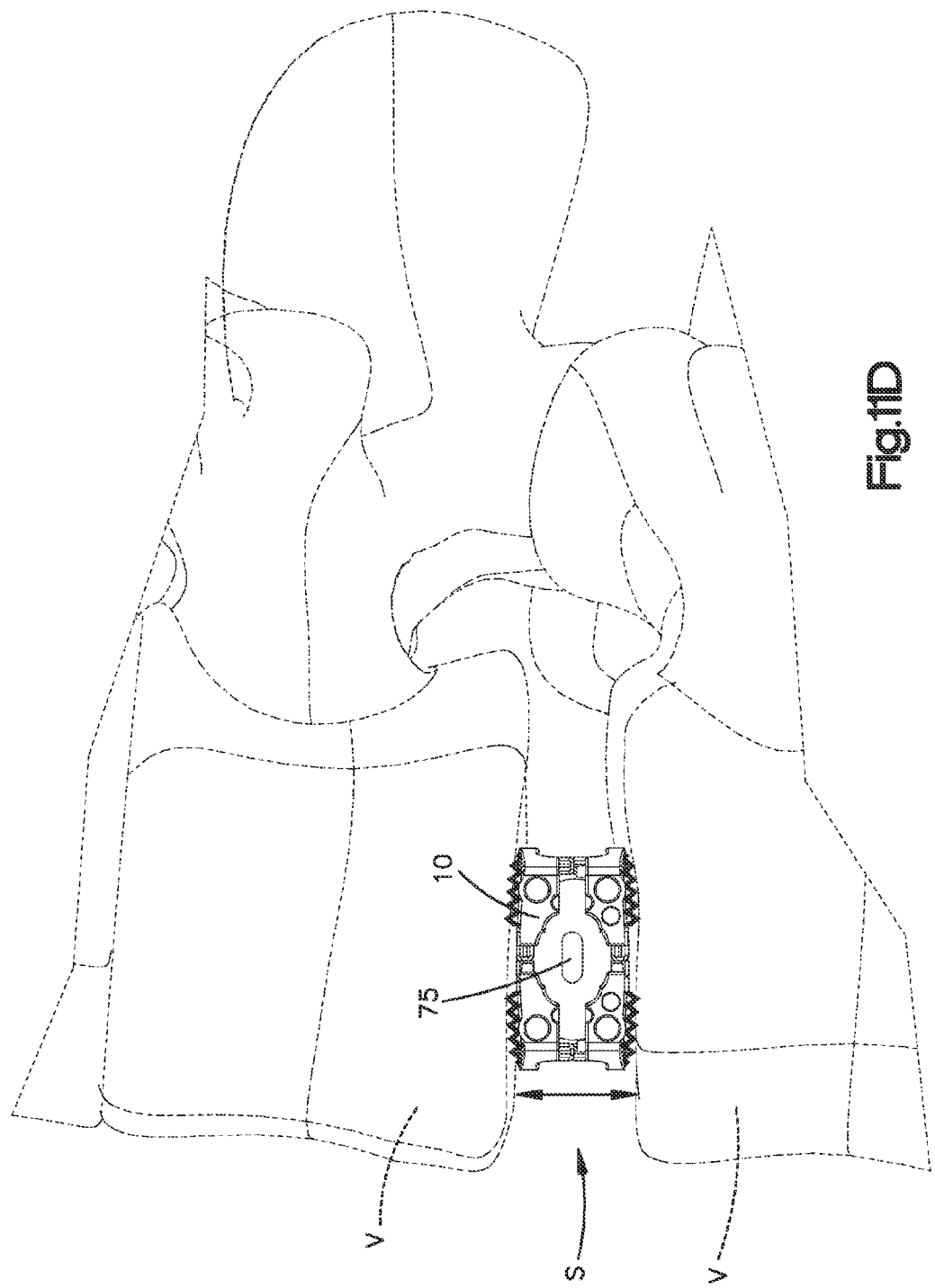

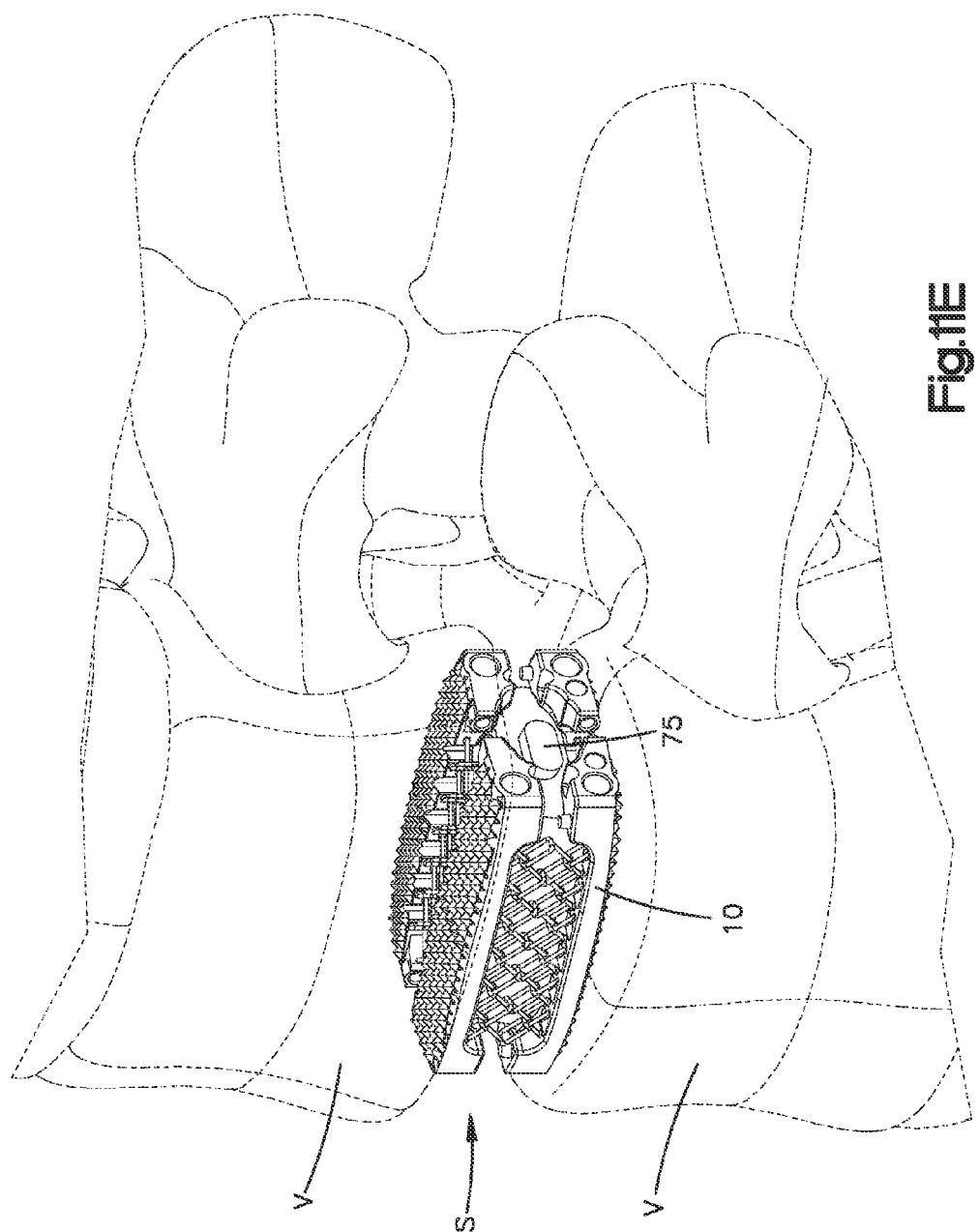

EXPANDABLE INTERVERTEBRAL IMPLANT AND ASSOCIATED METHOD OF MANUFACTURING THE SAME

CROSS-REFERENCE TO RELATED APPLICATIONS

This application is the National Stage of International Application No. PCT/US2009/031567, filed Jan. 21, 2009, which claims the benefit of U.S. Provisional Application No. 61/021,778, filed Jan. 17, 2008, the disclosures of which are incorporated herein by reference in their entireties for all purposes.

BACKGROUND OF THE INVENTION

People, especially elderly people, may suffer from osteoporosis. One aspect of osteoporosis may be the partial or complete collapse of the bony structure of the spine, which in turn can cause loss of vertebral height, fracture of a vertebral disc, facet and nerve impingement, etc. Collapse of the spine often results in, for example, pain, reduction of lung function, unbalanced stature, etc. One treatment option may be a surgical procedure to re-align the vertebra (e.g., to re-establish balanced curvature of the spine as well as the intervertebral disc space).

Re-alignment of a spine including a damaged vertebra or disc may be accomplished by replacing the damaged vertebra, disc or portions thereof with an intervertebral implant. That is, an intervertebral implant may be inserted into the intervertebral disc space of two neighboring vertebral bodies or into the space created by removal of portions of or the entire vertebral body after removal of damaged portions of the spine. Preferably, the intervertebral implant restores the spine, as much as possible, to a natural state, i.e. to restore the original height of the intervertebral disc or the series of vertebra and, thus, the original distance between the two neighboring or adjacent vertebral bodies or vertebral bodies in various levels of the spine.

Typically implantation of one or more intervertebral implants is not part of a treatment procedure for osteoporosis. One reason for this may be that intervertebral implants are often designed with high structural stiffness. Osteoporotic bone is usually brittle, thus increasing the risk of breaking a vertebral endplate during a surgery or implantation of an implant and the endplates may have a uneven surface. For example, a stiff implant may impact a point or small area of an uneven surface of the osteoporotic bone, thereby creating a stress concentration and potentially damaging the bone. Therefore, the incorporation of an intervertebral implant in certain cases, is contra-indicated for patients with osteoporotic bone. Another reason for not incorporating an intervertebral implant may be that the insertion approach for implanting an intervertebral implant is difficult and risky, especially in elderly patients.

Alternatively, rather than implanting an intervertebral implant, a surgeon may elect to perform a Vertebralplasty and/or Cavitoplasty procedure on the patient's spine. In an exemplary method of performing a Vertebralplasty and/or Cavitoplasty procedure, a protective sleeve or cannula may be inserted into the patient's body, adjacent to the patient's spine. The spine may then be re-aligned if fractured or re-fractured. Next cement is inserted into the spine to replace lost bone and/or to limit future cracks. After the hardening of the cement, the treated section of the spine may be re-aligned and the patient may then return to his or her daily activity. In a Cavitoplasty procedure, a cavity may be formed in one or more of the vertebral bodies for receiving a portion of the cement.

It would be desirable to construct an intervertebral implant that is relatively simple to insert into a patient's spine at a relatively small size and which is able to expand to restore the original height of the removed spinal material or to a height desired by a surgeon. It would also be desirable to construct an intervertebral implant that is adaptable to uneven surfaces of an osteoporotic vertebral bone to limit stress concentrations when the implant is expanded and contacts or applies pressure to a patient's endplate.

BRIEF SUMMARY OF THE INVENTION

The present invention relates to an expandable intervertebral implant. More particularly, a preferred embodiment of the present invention relates to an intervertebral implant that is laterally and vertically expandable in situ from a collapsed, non-expanded or first insertion configuration to a second expanded configuration. The expandable intervertebral implant preferably includes superior and inferior bone contacting members connected together via one or more expandable components such as, for example, a wire netting so that the implant is vertically expandable in the cranio/caudal direction. The superior and inferior bone contacting members preferably are formed by two or more bone contacting components connected together via one or more expandable components such as, for example, a wire netting so that the implant is laterally expandable in the lateral direction if implanted via an anterior approach or laterally expandable in the anterior-posterior direction if implanted via a lateral approach.

The present invention also relates to an associated method of inserting and sequentially expanding the intervertebral implant and an associated method of manufacturing the intervertebral implant such that the intervertebral implant can be manufactured as an integral component.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the expandable intervertebral implant, surgical method for implanting the intervertebral implant and manufacturing method for forming the intervertebral implant of the present application, there are shown in the drawings preferred embodiments. It should be understood, however, that the application is not limited to the precise arrangements and instrumentalities shown. In the drawings:

FIG. 6A illustrates a top perspective view of a first preferred embodiment of a link member that may be used to form wire netting that may be used in conjunction with the intervertebral implant shown in FIG. 1;

FIG. 6B illustrates a top plan view of the wire netting shown in FIG. 6A, the wire netting illustrated in an at least partially collapsed, non-expanded or first insertion configuration;

FIG. 6C illustrates a top plan view of the wire netting shown in FIG. 6A, the wire netting illustrated in the second expanded configuration;

FIG. 7 illustrates a top perspective view of a second preferred embodiment of a link member that may be used to form wire netting that may be used in conjunction with the intervertebral implant shown in FIG. 1;

FIG. 8 illustrates a top perspective view of a third preferred embodiment of a link member that may be used to form wire netting that may be used in conjunction with the intervertebral implant shown in FIG. 1;

FIG. 9 illustrates a top perspective view of a fourth preferred embodiment of a link member that may be used to form wire netting that may be used in conjunction with the intervertebral implant shown in FIG. 1;

FIGS. 11A-11E illustrate various perspective views of steps of an exemplary surgical method for laterally inserting the expandable intervertebral implant of FIG. 1 in accordance with one aspect of the preferred invention.

DETAILED DESCRIPTION OF THE INVENTION

Figure 1:
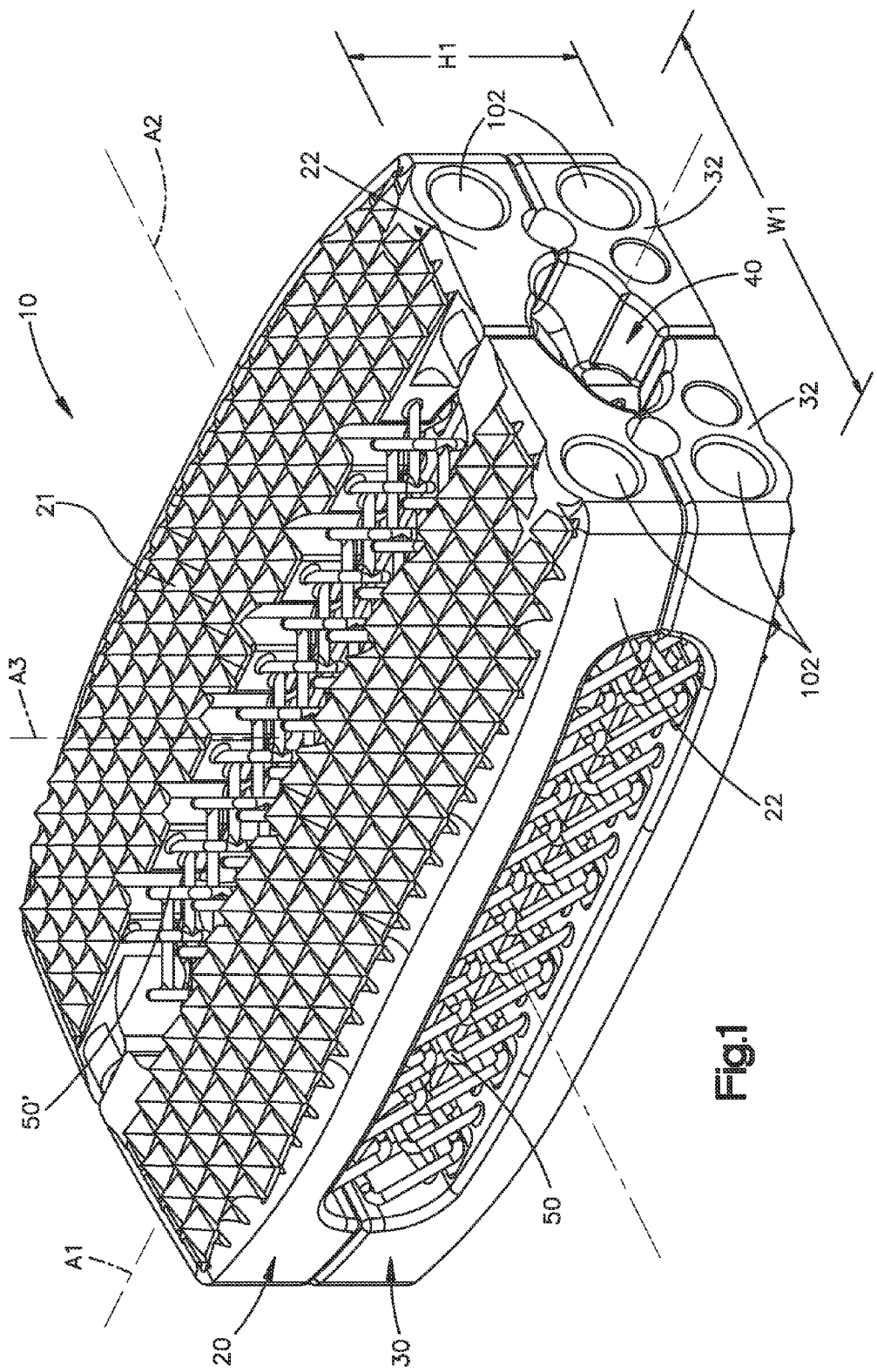
FIG. 1 illustrates a top perspective view of an exemplary intervertebral implant according to the present invention, the implant illustrated in the collapsed, non-expanded or first insertion configuration.
Figure 2:
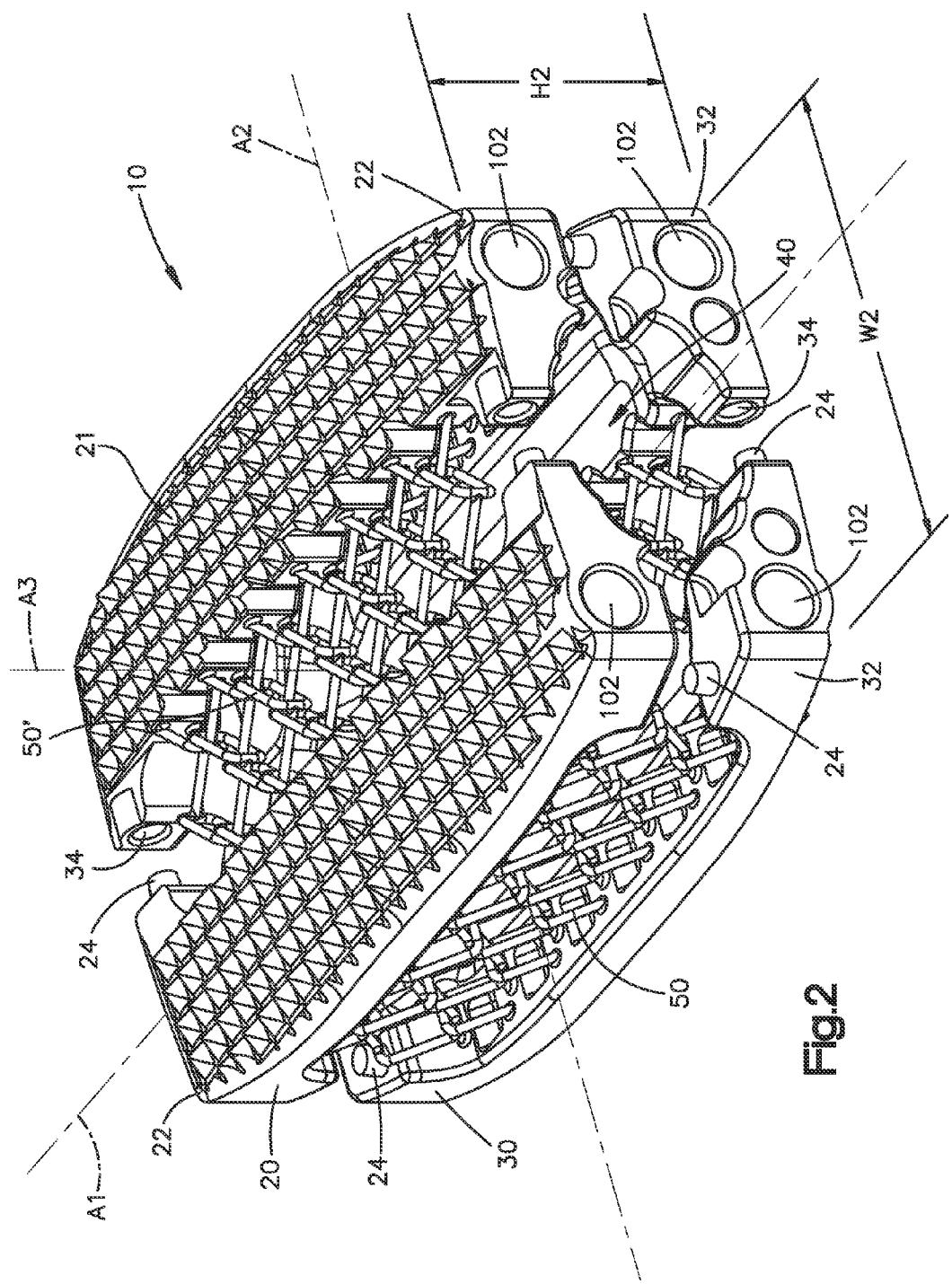
FIG. 2 illustrates a top perspective view of the intervertebral implant shown in FIG. 1, the implant illustrated in a second, expanded configuration.
Figure 3A:
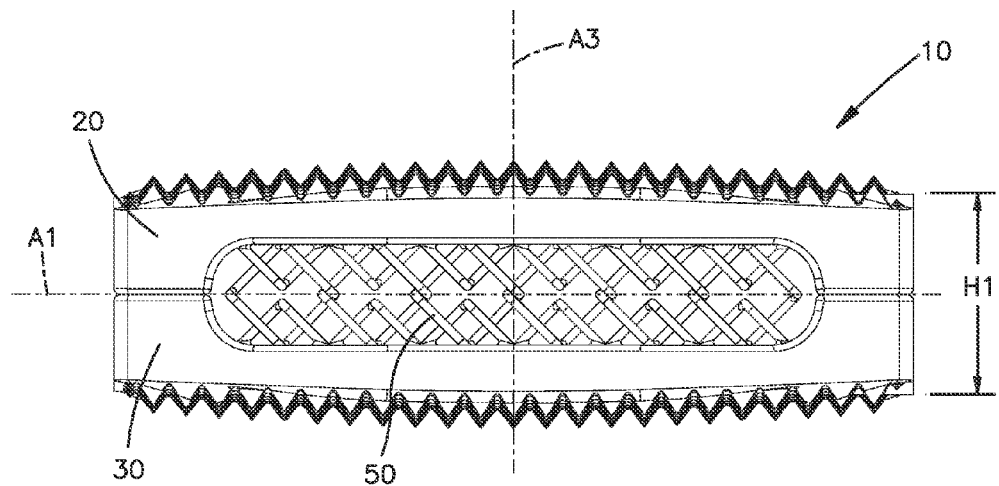
FIG. 3A illustrates a side elevational view of the intervertebral implant shown in FIG. 1, the implant illustrated in the collapsed, non-expanded or first insertion configuration.
Figure 3B:
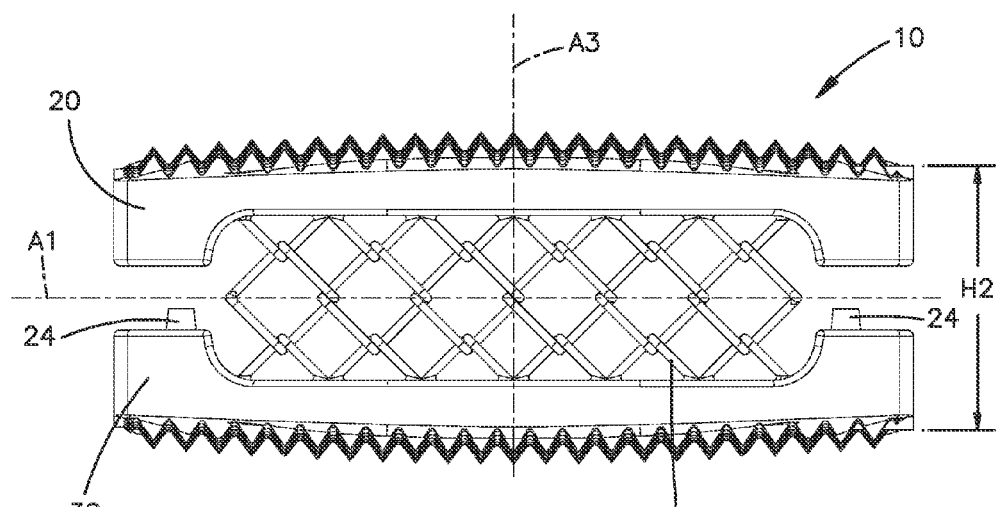
FIG. 3B illustrates a side elevational view of the intervertebral implant shown in FIG. 1, the implant illustrated in the second expanded configuration.
Figure 4A:
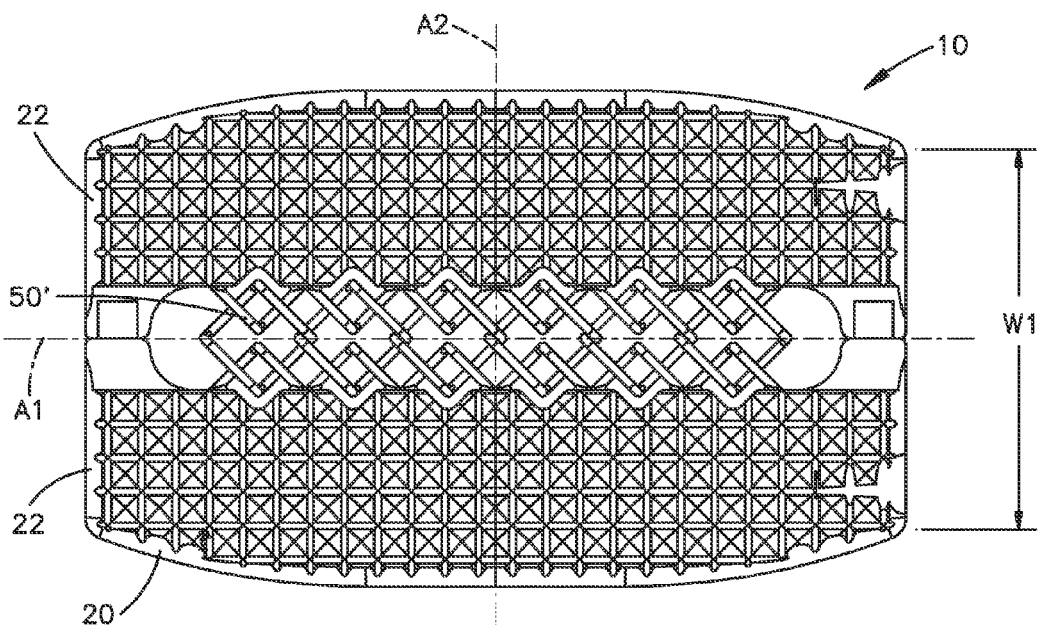
FIG. 4A illustrates a top plan view of the intervertebral implant shown in FIG. 1, the implant illustrated in the collapsed, non-expanded or first insertion configuration.
Figure 4B:
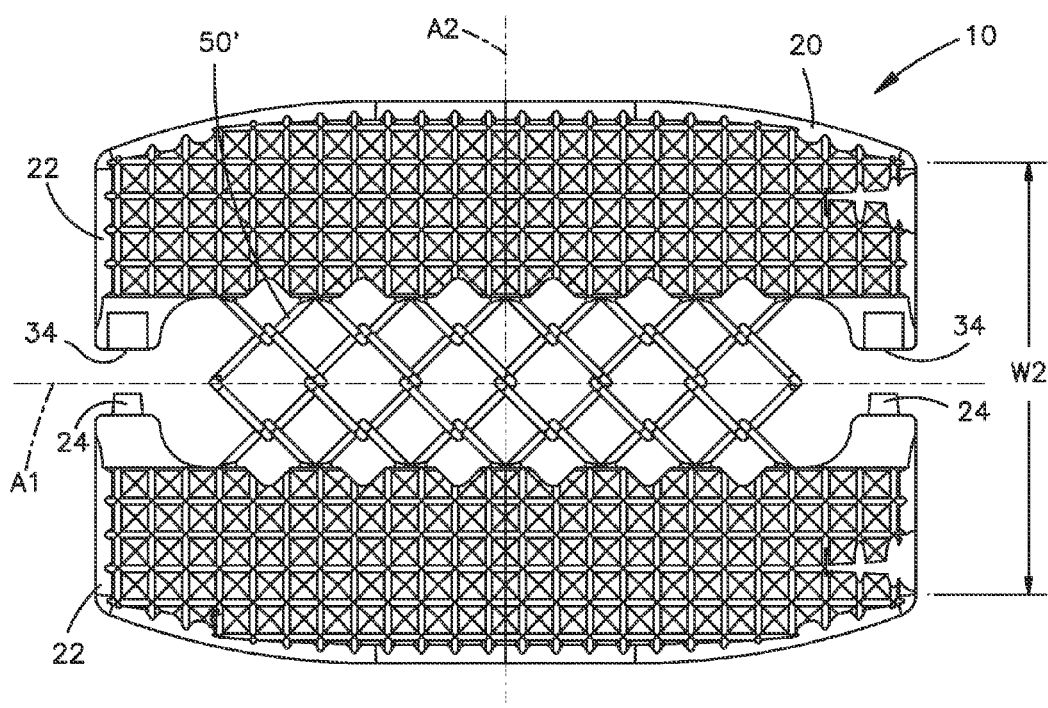
FIG. 4B illustrates a top plan view of the intervertebral implant shown in FIG. 1, the implant illustrated in the second expanded configuration.
Figure 5A:
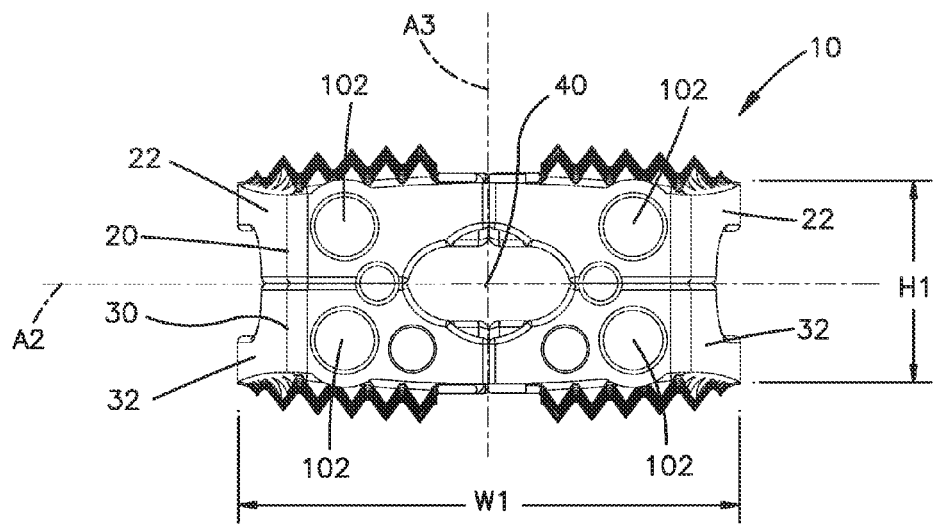
FIG. 5A illustrates a front elevational view of the intervertebral implant shown in FIG. 1, the implant illustrated in the collapsed, non-expanded or first insertion configuration.
Figure 5B:
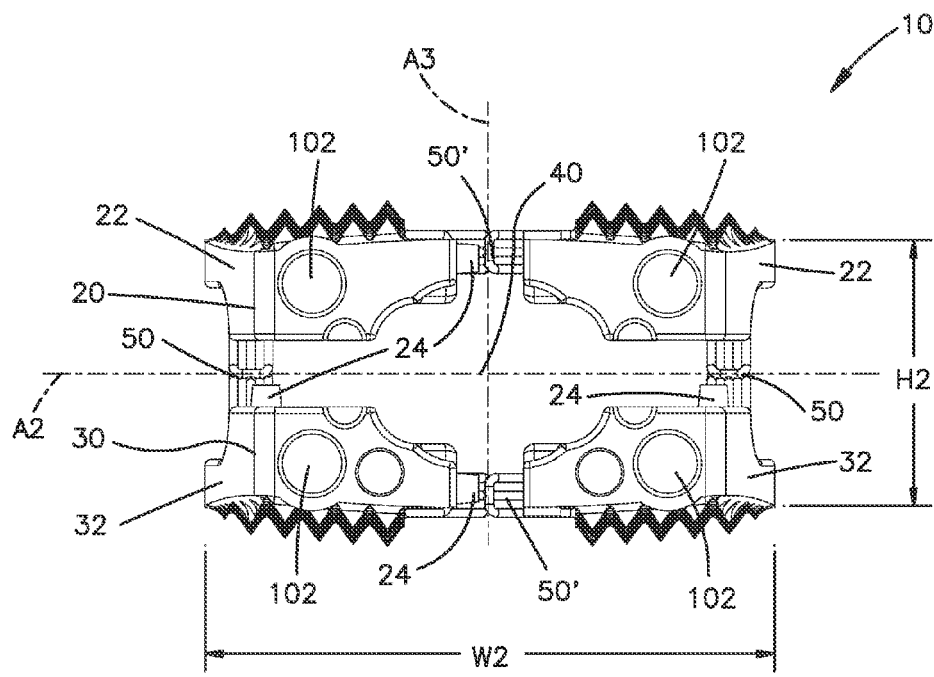
FIG. 5B illustrates a front elevational view of the intervertebral implant shown in FIG. 1, the implant illustrated in the second expanded configuration.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general preferred embodiments of the present invention are directed to (i) an expandable intervertebral implant 10 for implantation between or to replace damaged portions of adjacent vertebral bodies V in a patient's spine (for example, in the lumbar, thoracic or cervical regions), (ii) an exemplary surgical method for implanting the intervertebral implant 10 between adjacent vertebral bodies V in the patient's spine and (iii) an exemplary method of manufacturing the intervertebral implant 10. More specifically, the present invention is preferably directed to an expandable intervertebral implant 10 for total or partial disc or vertebral body V replacement or for nucleus replacement of an intervertebral disc space S. It should be appreciated that while the expandable intervertebral implant 10 of the present application will be described in connection with spinal disc replacement, one of ordinary skill in the art will understand that the implant 10 as well as the components thereof may be used for replacement of tissue in other parts of the body including, for example, knee, hip, shoulder, finger or other joint replacement or for bone augmentation.

Referring to FIGS. 1-5B, as will be described in greater detail below, the expandable intervertebral implant 10 is preferably used for intervertebral support of the spine for patients that require interbody fusion at one or more levels of the spine. The expandable intervertebral implant 10 is preferably implanted by a surgeon into the patient's body in a collapsed, non-expanded or first insertion configuration (as best shown in FIGS. 1, 3A, 4A and 5A), thereby allowing a smaller incision than is typically necessary for implantation of a non-expandable intervertebral implant (not shown). Implantation of the preferred expandable intervertebral implant 10 in the first insertion configuration may also make it easier to insert the implant 10 past structures that may inhibit a surgeon's access to the spine. The expandable intervertebral implant 10 allows surgeons to implant a larger intervertebral implant in the disc space S, generally without having to do an excessive amount of boney resection and soft tissue retraction. Once the implant 10 is inserted into the disc space S, the implant 10 may be expanded to a second expanded configuration (as best shown in FIGS. 2, 3B, 4B and 5B). More preferably, the implant 10 is expandable in the cranio/caudal direction to provide parallel and/or lordotic intervertebral distraction and in the lateral direction. That is, the expandable intervertebral implant 10 is preferably implanted by a surgeon into the patient's body in a collapsed, non-expanded or first insertion configuration wherein the implant has a first height $H_1$ and a first width $W_1$. Thereafter, once inserted into the disc space S, the implant 10 may be expanded to a second expanded configuration wherein the implant 10 has a second height $H_2$ and a second width $W_2$, wherein the second height $H_2$ and the second width $W_2$ are larger than the first height $H_1$ and the first width $W_1$, respectively.

The preferred expandable intervertebral implant 10 may, for example, fill the entire intervertebral disc space S to replace the entire intervertebral disc. Alternatively, a plurality of expandable intervertebral implants 10 may be used to fill the intervertebral disc space S. For example, two or more smaller expandable intervertebral implants 10 may be used to fill the intervertebral disc space S. Alternatively, the expandable intervertebral implant 10 may be sized and configured to only partially replace an intervertebral disc space S, such as for example, to replace a nucleus. In addition, the preferred intervertebral implant 10 may be configured to replace a disc and a portion of a damages vertebra V.

The expandable intervertebral implant 10 preferably includes a superior bone contacting member 20 for contacting a first, superior vertebra V, an inferior bone contacting member 30 for contacting a second, inferior vertebra V and a vertical wire netting or mesh 50 for interconnecting the superior and inferior bone contacting members 20, 30 with respect to one another. The vertical wire netting 50 preferably enables the superior and inferior bone contacting members 20, 30 to move (e.g., expand) in the cranial/caudal direction or generally away from each other during movement from the collapsed, non-expanded or first insertion configuration to the second expanded configuration when the implant 10 is inserted into the disc space S. The superior and inferior bone contacting members 20, 30 are sized and configured to contact at least a portion of the endplates of the superior and inferior vertebral bodies V, respectively, or to engage a surface of the superior and/or inferior vertebral bodies V remaining after damaged portions of the superior and/or inferior vertebrae V are removed from the spine. The superior and inferior bone contacting members 20, 30 preferably define a cavity 40 therebetween.

The superior bone contacting member 20 of the exemplary preferred embodiment is formed by two or more bone contacting components 22 interconnected by a lateral wire netting or mesh 50'. Similarly, the inferior bone contacting member 30 of the exemplary preferred embodiment is formed by two or more bone contacting components 32 interconnected by the lateral wire netting 50'. That is, the superior and inferior bone contacting members 20, 30 are each preferably constructed by a plurality of generally rigid bone contacting components 22, 32 separated by or interconnected by the lateral expandable wire netting 50' so that the bone contacting components 22, 32, which form the bone contacting members 20, 30, are moveable (e.g., expandable) with respect to one another. As shown, the bone contacting components 22, 32 preferably are in the form of one or more plates, more preferably an L-shaped plate, although other shapes are contemplated. However, the bone contacting members 20, 30 may be constructed as a single integral component, for example, if the implant 10 is constructed to expand only in the cranial/caudal direction. In addition, the superior and inferior bone contacting members 20, 30 may have convex-shaped surfaces wherein they contact the endplates of the vertebra V to conform to the shape of the endplates.

In this manner, by incorporating the vertical wire netting 50 between the superior and inferior bone contacting members 20, 30, the implant 10 is expandable from the collapsed, non-expanded or first insertion configuration wherein the implant 10 has a first height $H_1$ to the second expanded configuration wherein the implant 10 has a second height $H_2$, wherein the second height $H_2$ is larger than the first height $H_1$. Similarly, by incorporating the lateral wire netting 50' between the adjacent bone contacting components 22, 32, which form the superior and inferior bone contacting members 20, 30, respectively, the implant 10 is expandable from the collapsed, non-expanded or first insertion configuration wherein the implant 10 has a first width $W_1$ to a second expanded configuration wherein the implant 10 has a second width $W_2$, wherein the second width $W_2$ is larger than the first width $W_1$. That is, the lateral wire netting 50' preferably enables the bone contacting components 22, 32 to be laterally moveable (e.g., in the anterior-posterior or lateral direction depending on insertion procedure) with respect to one another along a lateral axis $A_2$ while the vertical wire netting 50 enables the superior and inferior bone contacting members 20, 30 to be vertically moveable with respect to one another along a vertical axis $A_3$. In addition, the vertical and lateral wire netting 50, 50' enables the superior bone contacting member 20 to move with respect to the inferior bone contacting member 30 along a longitudinal axis $A_1$. Thus, the vertical and lateral wire netting 50, 50' enables the implant 10 to conform its final shape in the second or expanded configuration to mate to the typically uneven surfaces of the endplates of the vertebral bodies V. In addition, the vertical and lateral wire netting 50, 50' enables the implant 10 to limit stress risers at contact points between the implant 10 and the vertebral bodies V thus making the preferred implant 10 applicable for insertion between osteoporotic bone.

That is, in the preferred embodiment, by forming the preferred implant 10 from four bone contacting components 22, 32 interconnected by vertical and lateral wire netting 50, 50', the superior and inferior bone contacting members 20, 30 of the implant 10 are preferably able to move in six degrees of freedom with respect to each other. Specifically, the superior and inferior bone contacting members 20, 30 are able to move longitudinally relative to each other along the longitudinal axis $A_1$, laterally relative to each other along the lateral axis $A_2$, vertically relative to each other along the vertical axis $A_3$, pivot or roll relative to each other about the longitudinal axis $A_1$, pivot or pitch relative to each other about the lateral axis $A_2$ and pivot or yaw relative to each other about the vertical axis $A_3$. Accordingly, the preferred implant 10 is able to conform its final shape in the second or expanded configuration to mate to the typically uneven surfaces of the endplates of the vertebral bodies V and limit stress risers at contact points between the implant 10 and the vertebral bodies V.

It should be noted that it is also envisioned that the superior and inferior bone contacting members 20, 30 may be formed of four or more bone contacting components 22, 32 interconnected by lateral wire netting 50' and longitudinal wire netting (not shown) so that the implant 10 is longitudinally moveable from a first length to a second length (not shown). Alternatively, the superior and inferior bone contacting members 20, may be formed of two bone contacting components 22, 32 interconnected by longitudinal wire netting (not shown) but not lateral wire netting 50' so that the implant 10 is longitudinally moveable from a first length to a second length (not shown) but not laterally moveable from the first width $W_1$ to the second width $W_2$.

The vertical wire netting 50 and the lateral wire netting 50', preferably enable approximately three tenths of a millimeter (0.3 mm) to approximately twelve millimeters (12 mm) of movement, although other amounts of movement are permissible as would be apparent to one having ordinary skill in the art. Further, the implant is not limited to having the generally rectangular or box-shaped configuration shown in FIGS. 1-12L, for example, the implant 10 may have a generally circular or cylindrical-shaped series of rings that form the superior and inferior bone contacting members 20, 30 separated by wire netting such that an inner ring may expand along the vertical axis A3 further than an outer ring to conform to a concave-shaped endplate.

Referring to FIGS. 6A-6C, a first preferred, exemplary embodiment of the vertical and/or lateral wire netting 50, 50' is formed by interconnecting a plurality of individual first link members 52. As shown, the plurality of individual first link members 52 may have a generally rectangular shape when at least partially expanded but are not so limited. Referring to FIG. 7, a second preferred exemplary embodiment of the lateral and/or vertical wire netting 50, 50' may be formed by interconnecting a plurality of individual second link members 52' wherein the plurality of individual second link members 52' have a generally trapezoidal shape when at least partially expanded but are not so limited. Referring to FIG. 8, a third preferred, exemplary embodiment of the vertical and/or lateral wire netting 50, 50' may be formed by interconnecting a plurality of individual third link members 52" wherein the plurality of individual think link members 52" have an alternate, second rectangular shape when at least partially expanded but are not so limited. Referring to FIG. 9, a fourth preferred, exemplary embodiment of the vertical and/or lateral wire netting 50, 50' may be formed by interconnecting a plurality of individual fourth link members 52'" wherein the plurality of individual fourth link members 52'" have an alternate, third rectangular shape when at least partially expanded but are not so limited. Alternatively, the vertical and/or lateral wire netting 50, 50' may have any other form or shape such as, for example, a plastically deformable material, mesh, stent, etc. so long as the vertical and/or lateral wire netting 50, 50' interconnects and enables the superior and inferior bone contacting members 20, and/or the superior and inferior bone contacting components 22, 32 to move with respect to one another. The preferred individual link members 52, 52', 52", 52'" are not limited to the generally rectangular or trapezoidal shapes and may take nearly any shape such as, for example, oval, circular, triangular, hexagonal, etc.

Figure 10A:
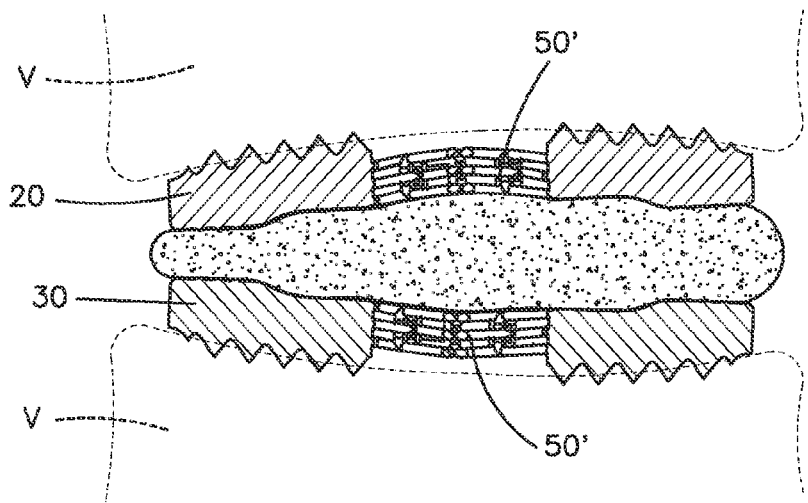
FIGS. 10A-10C illustrate various cross-sectional views of the intervertebral implant shown in FIG. 1, the superior and inferior bone contacting members incorporating wire netting so that the superior and inferior bone contacting members are able to adapt and/or conform to the endplates of the superior and inferior vertebral bodies V, respectively.
Figure 10B:
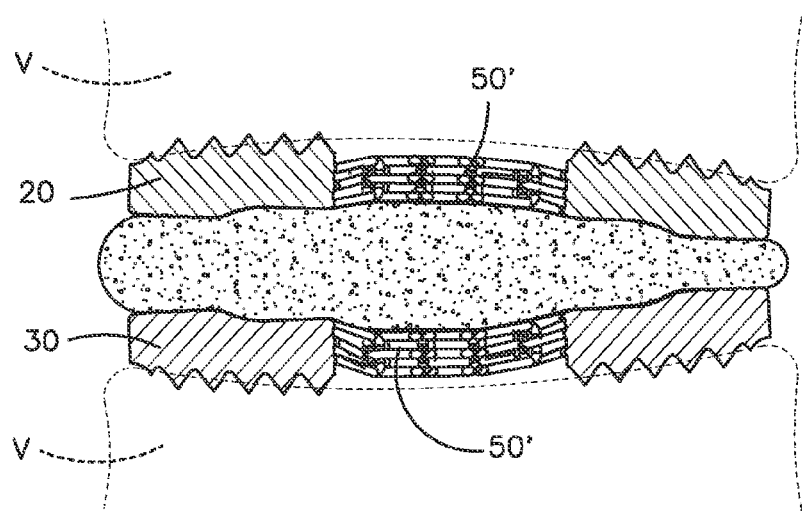
Figure 10C:
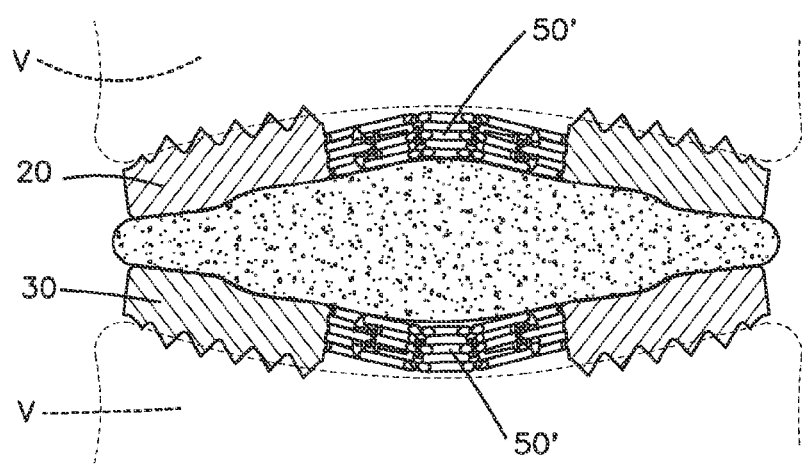

In addition, by forming or constructing the vertical and/or lateral wire-netting 50, 50' from a plurality of preferred individual first, second, third and/or fourth link members 52, 52', 52", 52'" the superior and/or inferior bone contacting components 22, 32 are able to tilt or generally move with respect to one another so that the superior and inferior bone contacting members 20, 30 are better able to conform to the configuration of the endplates of the adjacent vertebral bodies V. That is, as previously described above, by forming the preferred implant 10 from four bone contacting components 22, 32 interconnected by vertical and lateral wire netting 50, 50', the flexible of the vertical and/or lateral wire netting 50, 50' enables the superior and inferior bone contacting members 20, 30 of the implant 10 to move in six degrees of freedom with respect to each other so that the implant 10 and more particularly the superior and inferior bone contacting members 20, 30 are better able to adapt and/or conform to the anatomical shape of the endplates of the superior and inferior vertebral bodies V, respectively. As illustrated in FIGS. 10A-10C, the superior and inferior bone contacting components 22, 32 are better able to adapt and/or conform to the endplates of the superior and inferior vertebral bodies V, respectively, due to the inherent flexibility or adaptability of forming the superior and inferior bone contacting members 20, 30 from multiple components 22, 32 interconnected by a flexible wire netting 50, 50'. Thus, in use, the lateral wire netting 50' enables the superior bone contacting components 22 to move with respect to one another and enables the inferior bone contacting components 32 to move with respect to one another such that the lateral wire netting 50' enables the superior and inferior bone contacting members 20, 30 to adapt and/or conform to the endplates of the superior and inferior vertebral bodies V, respectively.

The preferred implant 10 also includes a cavity 40 located between the superior and inferior bone contacting members 20, 30. The cavity 40 is preferably sized and configured to receive a filling material (not shown) and/or a balloon 75, an expansion sack, an expansion bag, etc. (collectively referred to herein as an "expansion member"). The expansion member 75 is preferably sized and configured to be received within the cavity 40 in order to limit any filling material from overflowing and escaping from the cavity 40. More preferably, as will be described in greater detail below, once the implant 10 has been implanted and positioned, the expansion member 75 is preferably inserted into the cavity 40. Thereafter, the filling material may be inserted into the expansion member 75, expanding the expansion member 75 so that the implant 10 is expanded from the collapsed, non-expanded or first insertion configuration to the second expanded configuration. Once inserted, the filling material preferably hardens or is cross-linked in order to support the implant 10 in the second expanded configuration. Alternatively, the filling material may not harden and may partially harden into a gel-like material or may retain a flowable or liquid state and become sealed in the expansion member 75.

It should be noted that expanding of the expansion member 75 may or may not cause distraction of the adjacent vertebral bodies V. However, the flexibility of the expansion member 75 and the sequential hardening of the filling material preferably provide a geometrically adapted restoration of the intervertebral disc space S. Alternatively, the filling material may remain in a gel and/or liquid state and may be sealed in the expansion member 75. In addition, as will be generally appreciated by one of ordinary skill in the art, the expansion member 75 may be inserted into the cavity 40 prior to implantation of the implant 10, the filling material may be injected into the expansion member 75 prior to implantation of the implant 10, the expansion member 75 may be integrated with or coupled to the implant 10, and/or the expansion member 75 may be omitted entirely.

Moreover, it should be understood that the superior and inferior bone contacting members 20, 30 may include any number of bone contacting components 22, 32 and interconnecting lateral wire netting 50' such as, for example, three bone contacting components 22, 32 interconnected by two lateral wire nettings 50'. It is also envisioned that the implant 10 may include one or more intermediate components (not shown) between the superior and inferior bone contacting members 20, 30. The intermediate components may be coupled to the superior and inferior bone contacting members 20, 30 via the vertical wire netting 50. Moreover, it is also envisioned that the implant 10 may include the vertical wire netting 50 to enable cranio/caudal expansion without incorporating the lateral wire netting 50'. Alternatively, the implant 10 may include the lateral wire netting 50' to enable lateral expansion without incorporating the vertical wire netting 50.

The superior and inferior bone contacting members 20, 30 may include means for increasing the stability of the implant 10, such as, for example, one or more projections, one or more roughened surfaces, one or more undulating structures, one or more ridges, one or more keels, etc. Preferably, the superior and inferior bone contacting members 20, 30 include a plurality of teeth 21 for increasing the stability of the implant 10.

The implant 10 may also include a mechanism or feature for engaging an implant insertion instrument (not shown). The mechanism or feature for engaging the insertion instrument may take on any form now or hereafter known including, for example, one or more bores 102 for receiving one or more projections (not shown) formed on the implant insertion instrument, one or more projections (not shown) for engaging one or more bores (not shown) formed on the implant insertion instrument, one or more channels (not shown) for receiving one or more tips formed on the implant insertion instrument, one or more threaded bores (not shown) for receiving one or more threaded shafts or screws, etc.

The implant 10 may also include a mechanism or features for reducing and/or preventing shearing or dismantling of the implant 10 during insertion such as, for example, the superior and inferior bone contacting members 20, 30 may include interconnecting projections 24 and bores 34 for temporarily securing the implant 10 in its collapsed or insertion configuration.

The superior and inferior bone contacting members 20, 30 may be formed from any biocompatible material including, but not limited to, a metal, such as, for example, cobalt-chromium-molybdenum (CCM) alloys, titanium, titanium alloys, stainless steel, aluminum, etc., a ceramic such as, for example, zirconium oxide, silicone nitride, etc., an allograft, an autograft, a metal-allograft composite, a polymer such as, for example, polyaryl ether ketone (PAEK), polyether ether ketone (PEEK), polyether ketone ketone (PEKK), polyetherketone (PEK), polyetherketone ether-ketone-ketone (PEK-EKK), etc. The polymers may be reinforced with a fiber such as, for example, a carbon fiber or other thin, stiff fiber.

The superior and inferior bone contacting members 20, 30 may also be coated in order to enhance their osteo-conductive properties. For example, the bone contacting members 20, 30 may be coated with an etching, anodization, an anodic plasma chemical process, electrolytic deposition, plasma spraying, a thin layer of titanium (Ti) via a physical or chemical vapor deposition process, an anodic plasma chemical surface treatment incorporating, for example, Ca and/or P in the Ti-Oxide surface layer or via a Ti or HA plasma spray, etc.

The expansion member 75 may be manufactured from any biocompatible material including, but not limited to, a polyurethane, a polycarbonate urethane, a poly carbonate-silicone urethane copolymer, polyamine, polyethylene terephthalate (PET), polycaprolactone, etc.

The filling material may be any biocompatible material known in the art and may be a rigid or elastic material. The filling material may be comprised of, for example, a bone cement, a hydrogel, a polyvinyl alcohol, a sodium polyacrylate, an acrylate polymer, a methyl-methacrylate, a co-polymer with an abundance of hydrophilic groups, p-vinyl pyrolidone, polyethyleneimine, etc., a setting or curing hydrogel based co-polymer such as, for example, polyethyleneimine, poly(diethylaminoethyl methacrylate), poly(ethylaminoethyl methacrylate), etc., a thermally setting hydrogel based co-polymers, such as, for example, poly-N-isopropylacrylamide with polyethylene glycol, copolymers of polyethylene oxide and polyphenelylene oxide, copolymers of polyethylene glycol and polyactides, etc., an ionic setting hydrogel such as, for example, ethylacrylate, methacrylic acid, 1,4-butanediacrylate, etc., or a PCU, PCU-silicone co-polymer, silicone or other non-resorbable pure or elastic co-polymer (e.g., PCU's silicone end group modified PU's, RTV curing siloxane based elastomers, etc.).

Exemplary Method of Inserting the Intervertebral Implant

The expandable intervertebral implant 10 may be inserted within the targeted intervertebral disc space S by any means, method, or approach now or hereafter known in the art including, but not limited to, via anterior, lateral, posterior, anterior-lateral, or posterior-lateral approaches, etc. Preferably, the implant 10 is implanted using a minimally invasive technique. Alternatively, the implant 10 may be implanted via an open incision, as would be appreciated by one having ordinary skill in the art.

Figure 11A:
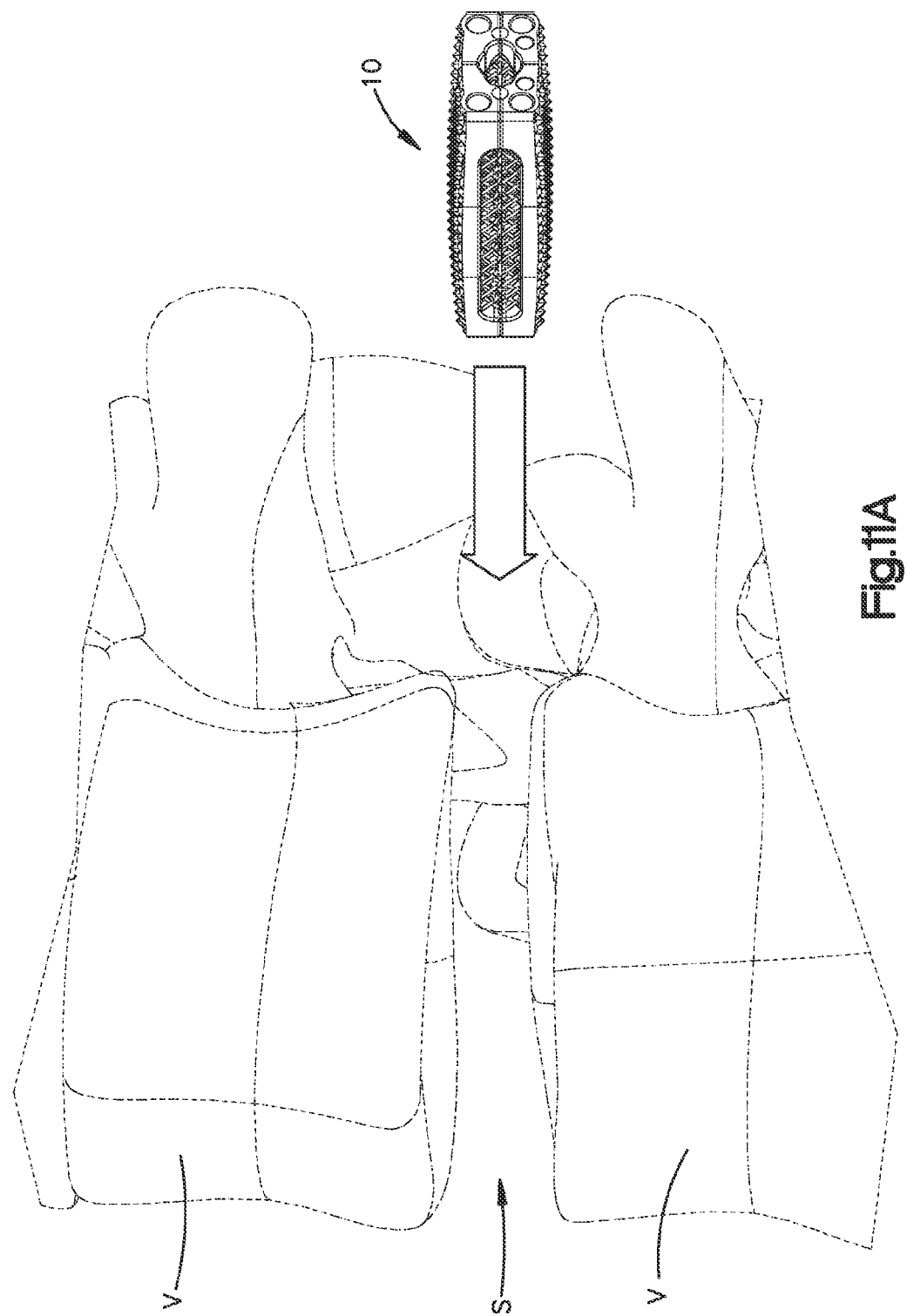
Figure 11B:
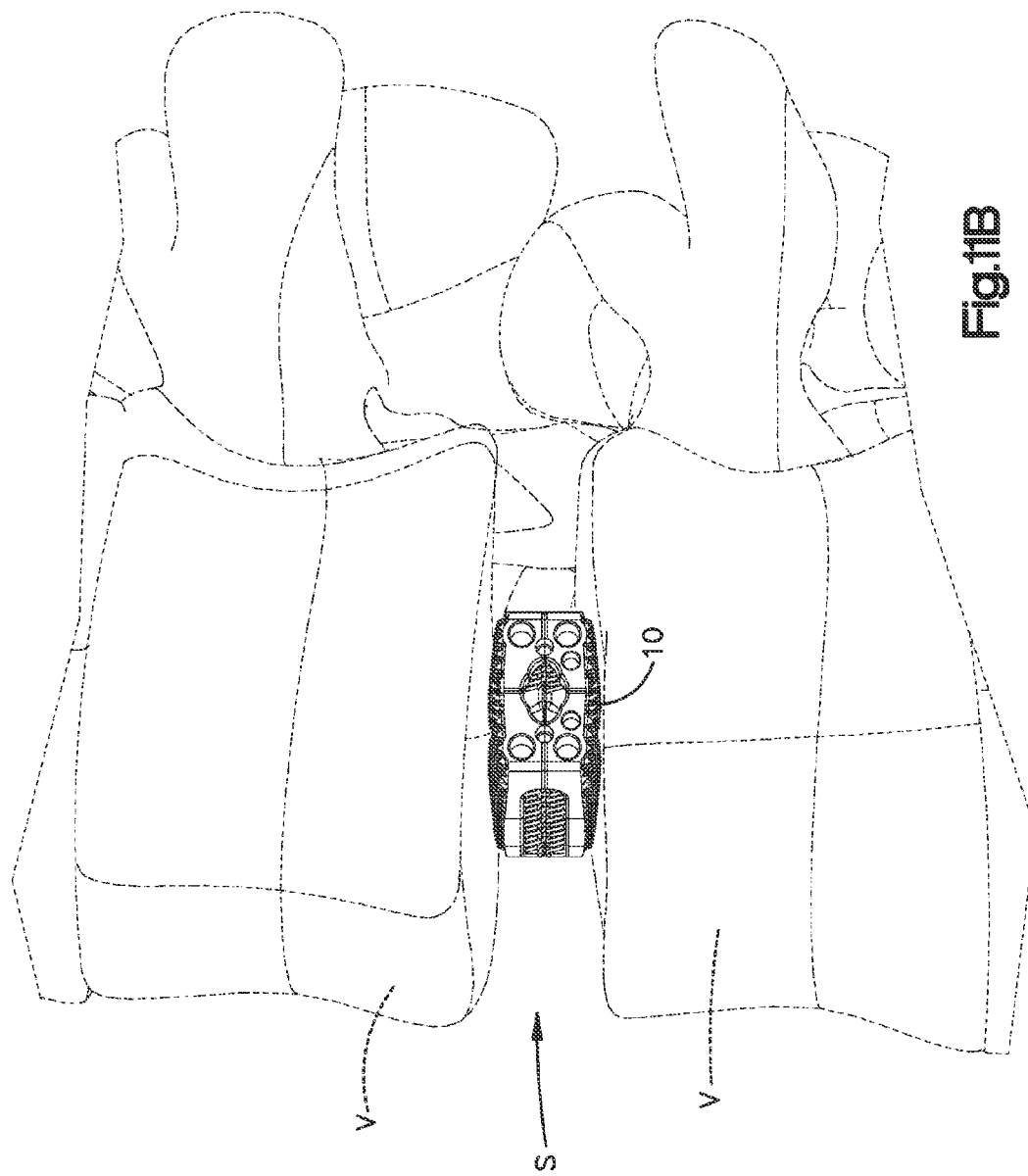
Figure 12A:
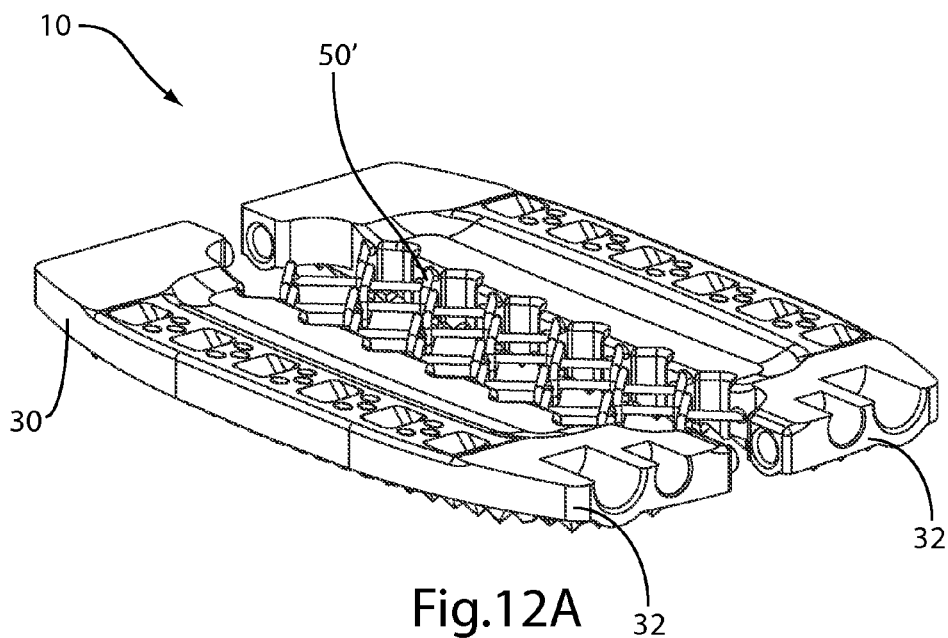
FIGS. 12A-12L illustrate various top, perspective views of steps of an exemplary method for manufacturing the expandable intervertebral implant of FIG. 1 in accordance with one aspect of the preferred invention.
Figure 12B:
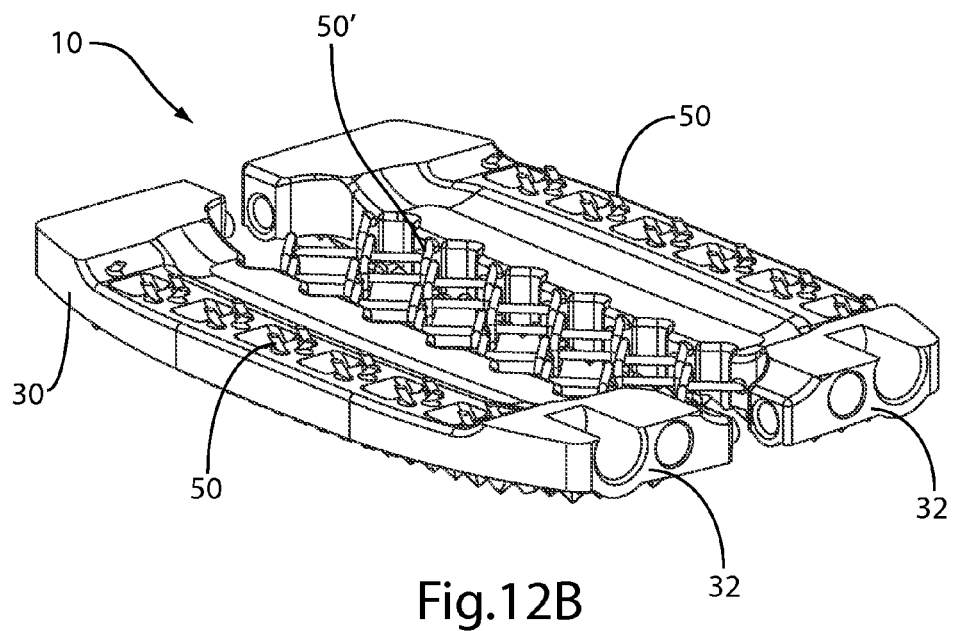
Figure 12C:
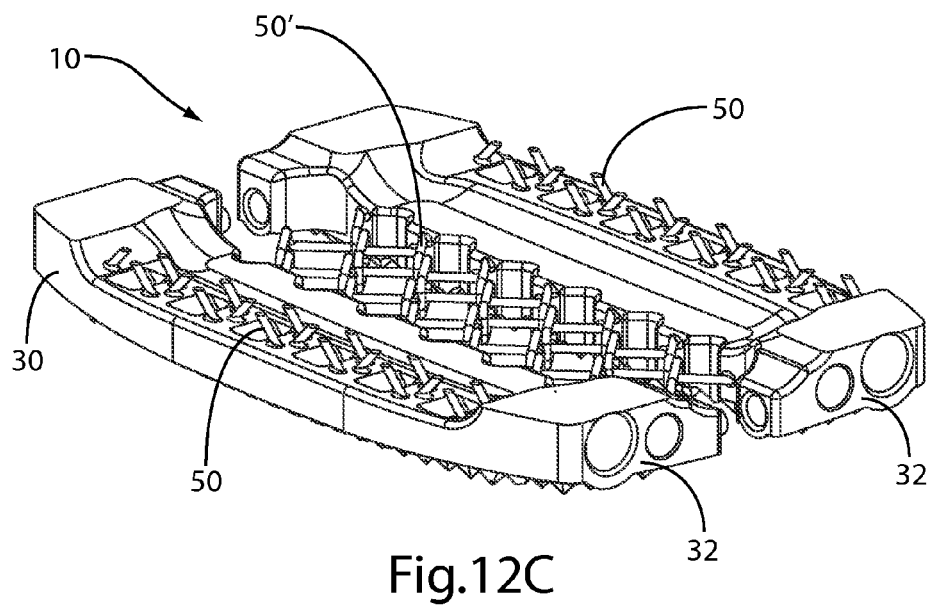
Figure 12D:
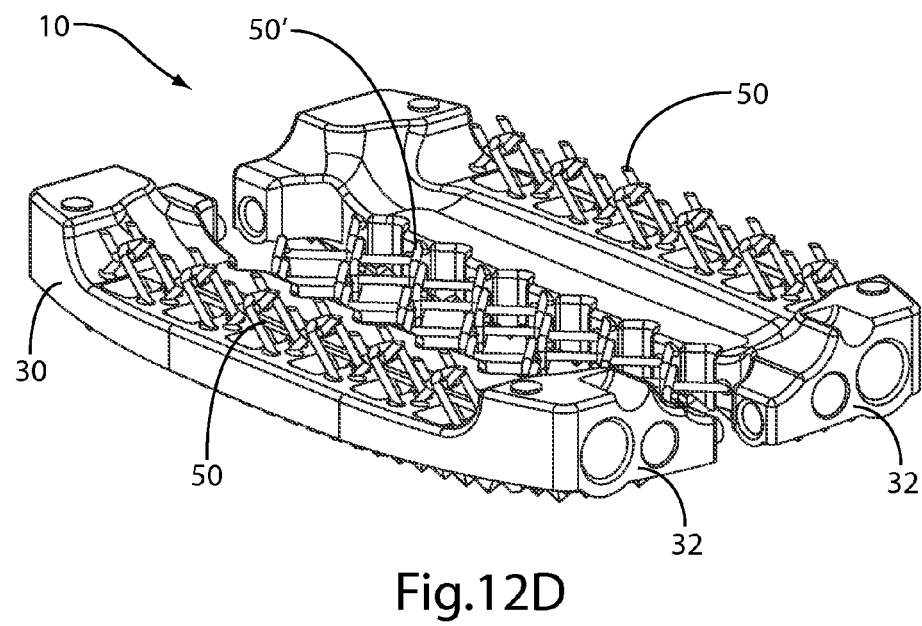
Figure 12E:
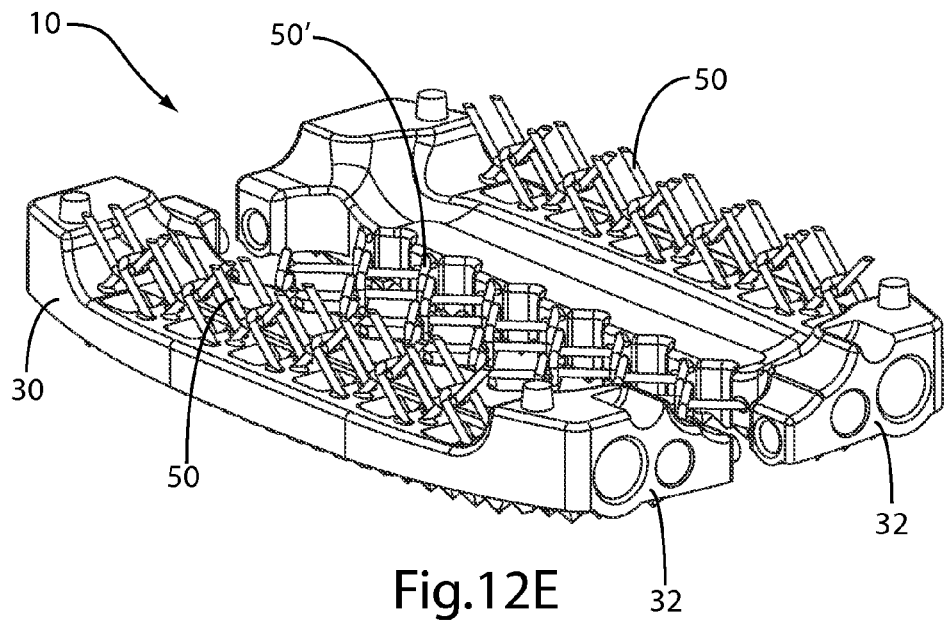
Figure 12F:
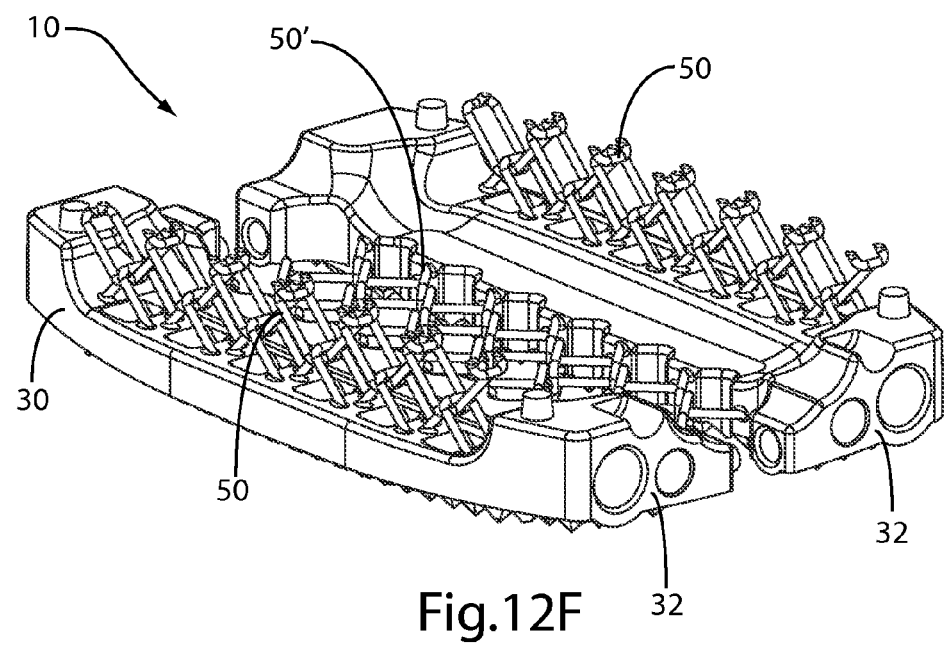
Figure 12G:
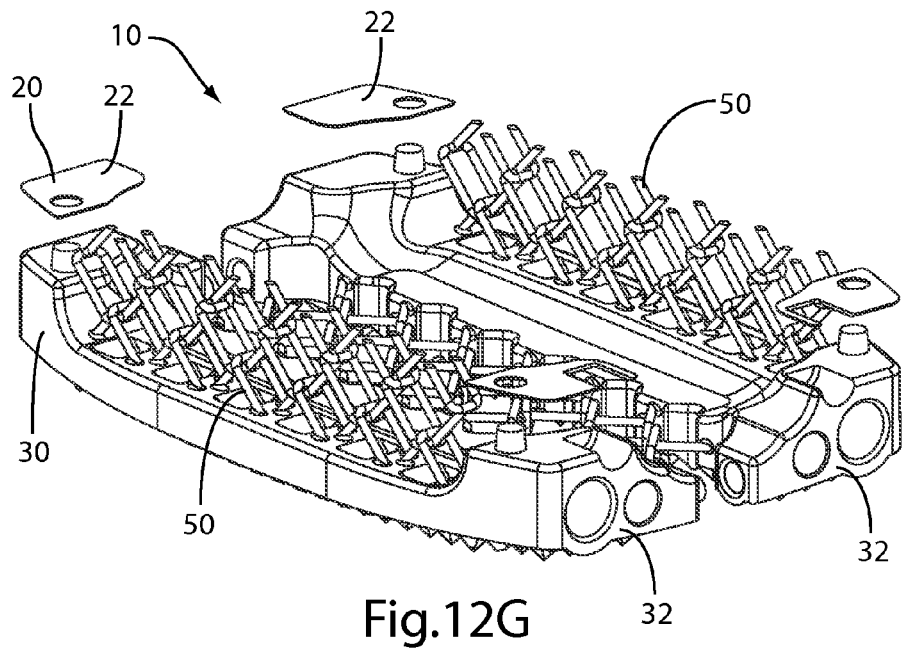
Figure 12H:
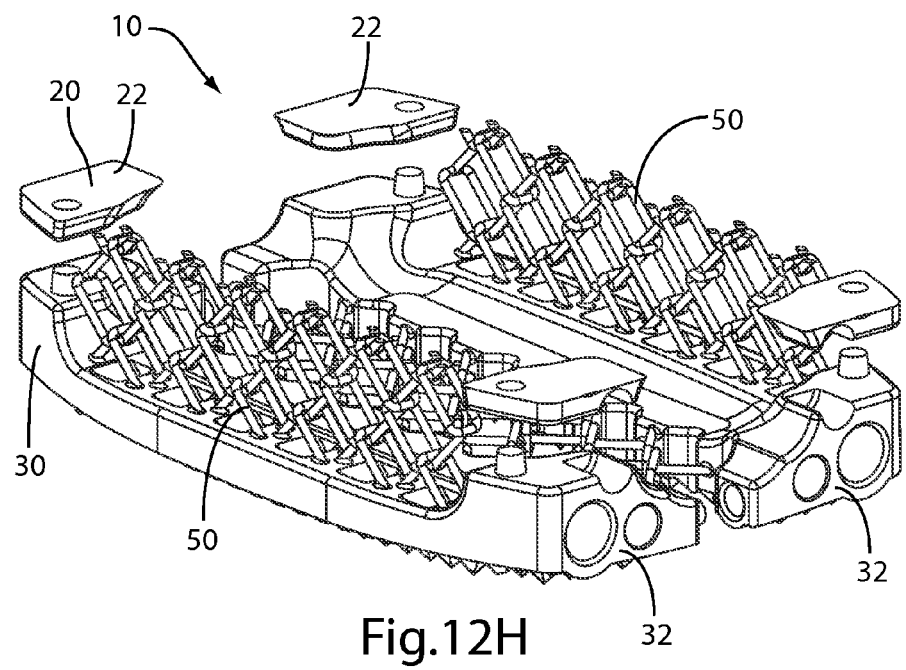
Figure 12I:
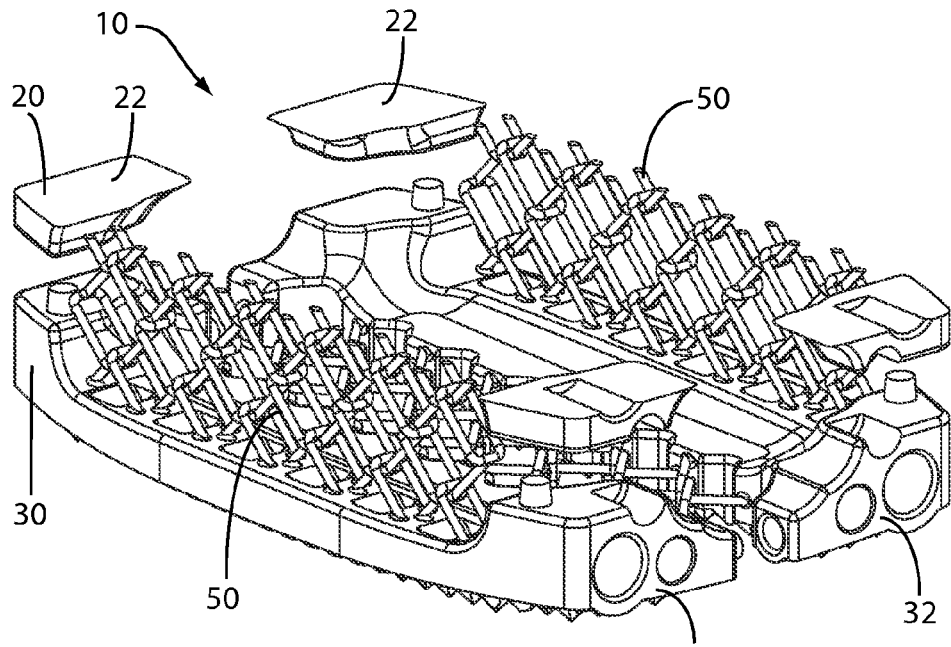
Figure 12J:
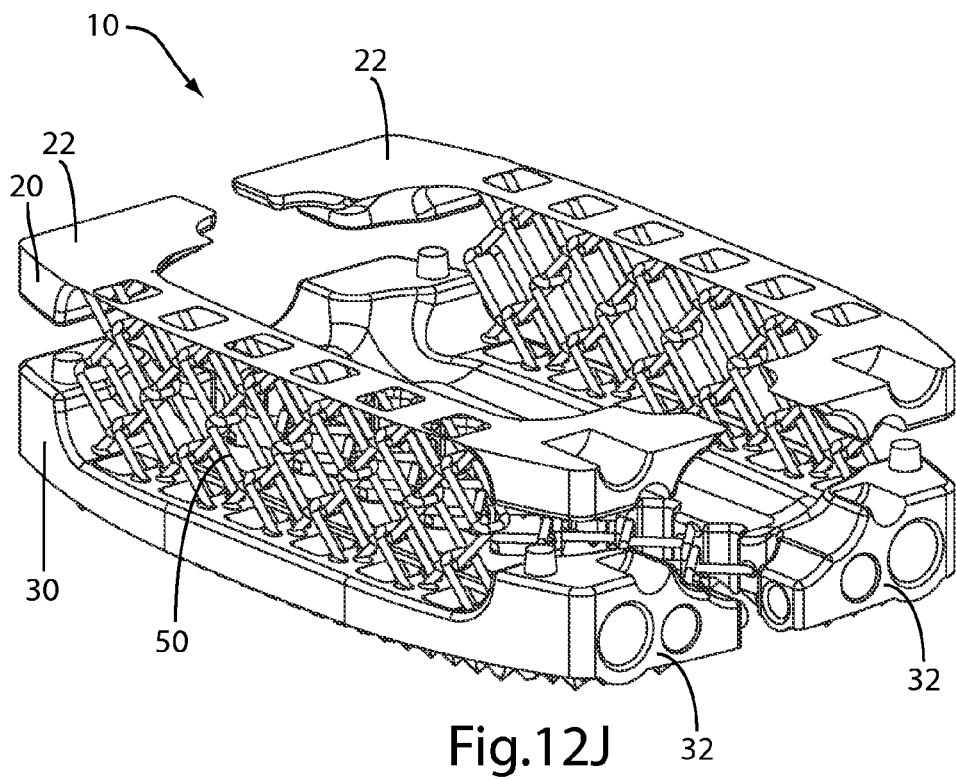
Figure 12K:
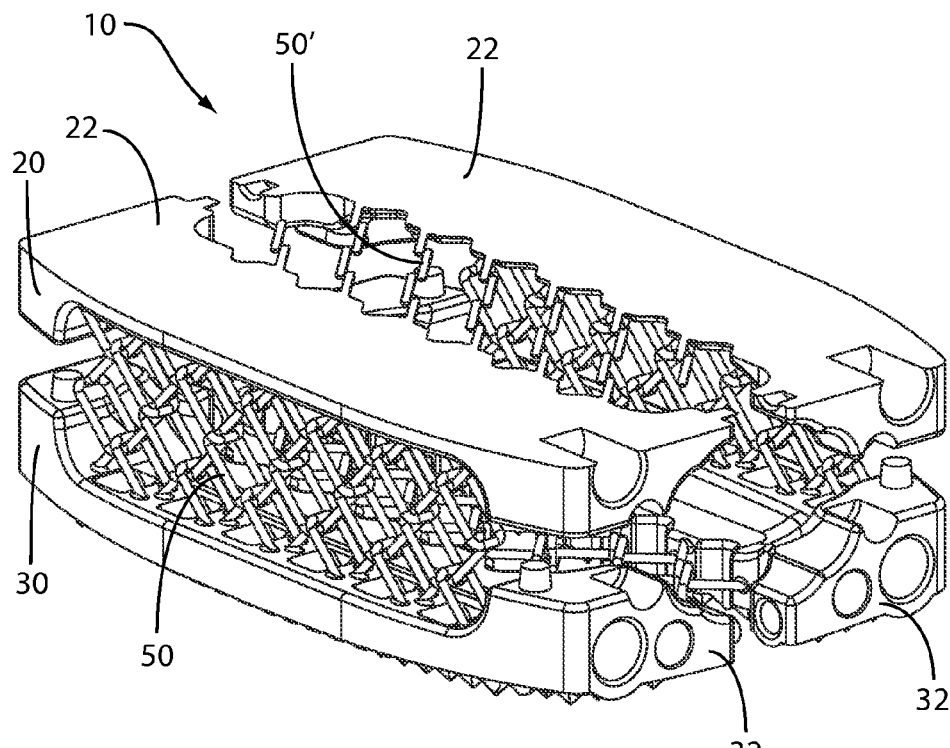
Figure 12L:
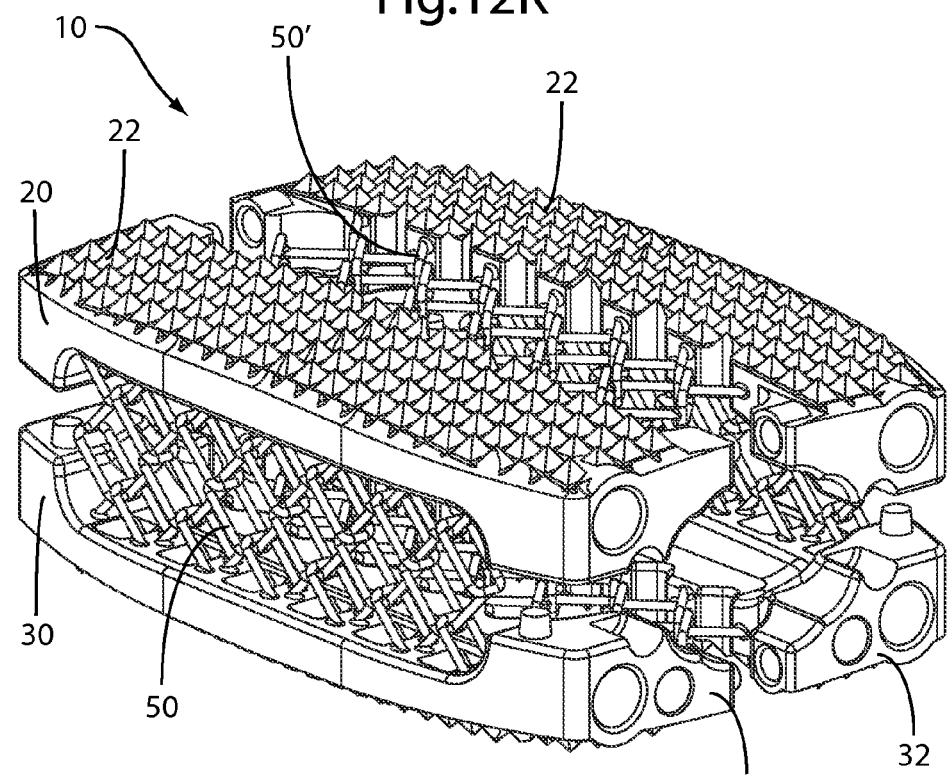

Referring to FIGS. 11A-11E, in one exemplary method of inserting the implant 10 via a lateral approach, the implant 10 is inserted into the intervertebral disc space S between adjacent superior and inferior vertebral bodies V via an insertion instrument (not shown). As illustrated in FIG. 11A, the implant 10 is preferably inserted into the intervertebral disc space S in the collapsed, non-expanded or first insertion configuration following a preferably minimal incision through the skin to the disc space S. As illustrated in FIG. 11B, the implant 10 is preferably positioned within the intervertebral disc space S at least partially in a posterior direction in order to generally keep the motion segment in balance. More preferably, the implant 10 should be positioned so that the implant 10 engages the stronger peripheral aspects of the adjacent vertebral bodies V. Once the implant 10 has been properly positioned in its desired location, as illustrated in FIG. 11C, the implant 10 is preferably laterally expanded in the anterior-posterior direction (in the lateral direction if the implant 10 was inserted via an anterior or posterior approach) via a surgical instrument (not shown). Alternatively, the implant 10 may be inserted with the expansion member or balloon 75 therein and laterally expanded via the expansion member 75. Preferably, the implant's position should be checked at this point to ensure preferred positioning. Once the position of the implant 10 is verified based generally on surgeon preference and/or physiology, as illustrated in FIG. 11D, the expansion member 75 is inserted and positioned within the cavity 40 formed in the implant 10 via an insertion instrument (not shown). The implant 10 may be slightly expanded via the implant insertion instrument in order to ease insertion of the expansion member 75 within the cavity 40, if necessary. Next the expansion member 75 is filled with a filling material, which causes the implant 10 to expand in the cranio/caudal direction, preferably resulting in the implant 10 firmly penetrating into the endplates of the adjacent superior and inferior vertebral bodies V. Due to the adaptability of the vertical and/or lateral wire netting 50, 50', the superior and inferior bone contacting members 20, 30 of the implant 10 may substantially mate to the typically uneven surfaces of the endplates of the superior and inferior vertebral bodies V, respectively. For example, the individual bone contacting members 22, 32 may move linearly relative to each other along the longitudinal, lateral and/or vertical axes A1, A2, A3 and may pivot relative to each other about the longitudinal, lateral and/or vertical axes A1, A2, A3 such that the shape of the implant 10 in the expanded configuration conforms to the anatomical shape of the pre-existing endplates of the vertebrae V. Specifically, each of the bone contacting members 22, 32 are movable relative to each other in six degrees of freedom to permit the individual components to adapt their final position to the patient's anatomy, thereby reducing stress risers that may develop when an implant is unable to conform to the shape of the anatomy.

Exemplary Method of Manufacturing the Intervertebral Implant

The preferred expandable intervertebral implant 10 may be manufactured by any means and/or method now or hereafter known in the art including, but not limited to, by manufacturing each of the bone contacting members 20, 30 as separate and distinct components and then coupling each of the components to vertical and lateral wire netting 50, 50', as required.

Preferably, however, the implant 10 is formed as an integral implant manufactured via a layer-wise or layer by layer manufacturing process. For example, referring to FIGS. 12A-12L, the implant 10 preferably is manufactured via a selective laser melting process. The metal components are preferably set up in layers, similar to a stereo-lithograph. In use, a thin layer of metal powder is applied to a platform. The powder is then locally melted by, for example, a laser beam. The platform is then lowered by a defined layer height. Another thin layer of metal powder is then applied. The second layer of powder is then locally melted. This process is repeated until the implant 10 is complete. The ability to manufacture the implant 10 as a single or integral component or part permits the manufacture of continuous loops or solid vertical and lateral wire netting 50, 50' between the bone contacting components 22, 32. In contrast, alternate techniques for constructing the vertical and lateral wire netting 50, 50' may require joining together of ends of the wires to construct the preferred first, second, third and fourth link members 52, 52', 52", 52'".

Alternatively, the implant 10 may be manufactured via a selective laser sintering process. Generally, the laser sintering process follows the same steps as the selective laser melting process described above. However since sintering is performed below the melting point of the substrate material, the laser sintering process allows the original metal powder to be mixed with a binding agent. A steam stripping process may be used after the laser sintering process. Using the laser sintering process, combinations of metals as well as micro-porous structures can be manufactured. The laser sintering process may also be used in connection with thermoplastic polymers which do not have any specific melting point but rather have a transition zone between a glass transition temperature and a melt mass temperature.

While laser melting and sintering processes have been described, other manufacturing methods are contemplated including, but not limited to, other methods of curing or sintering such as, for example, the use of ultrasonic or ultraviolet rays.

Features described herein may be used singularly or in combination with other features. In addition, features disclosed in connection with one embodiment may be interchangeable with a feature or features disclosed in another embodiment. Therefore the presently disclosed embodiments are to be considered as illustrative and not restrictive, the scope of the invention being indicated by the appended claims, and not limited to the foregoing description.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

The invention claimed is:

1. An expandable intervertebral implant defining a superior bone contacting surface, an inferior bone contacting surface spaced apart from the superior bone contacting surface along a vertical direction, the expandable intervertebral implant comprising:
   a first bone contacting member;
   a second bone contacting member positioned relative to the first bone contacting member along the vertical direction or a lateral direction that is substantially perpendicular to the vertical direction; and
   at least one expandable wire netting that connects the first bone contact member to the second bone contacting member,
   the at least one expandable wire netting comprising a plurality of interconnected individual link members, wherein adjacent link members are moveable relative to each other such that the bone contacting members are moveable relative to each other along at least the vertical direction or the lateral direction to expand the implant from a first insertion configuration to a second expanded configuration.

2. The implant of claim 1, wherein the plurality of individual link members have a rectangular shape.

3. The implant of claim 1, wherein the plurality of individual link members have a trapezoidal shape.

4. The implant of claim 1, wherein the first bone contacting member is a superior bone contacting member and the second bone contact member is an inferior bone contacting member spaced from the superior bone contacting member along the vertical direction, the implant further comprising:
   a cavity defined between the superior bone contacting member and the superior bone contacting member; and
   an expansion member insertable in the cavity, the expansion member capable of receiving a filling material so that injection of the filling material into the expansion member permits the wire netting interconnecting the superior and inferior bone contacting members to expand, thereby moving the superior bone contacting member with respect to the inferior bone contacting member such that the implant vertically expands from the first height to the second height.

5. The implant of claim 4, wherein the superior and inferior bone contacting members include one or more bores for engaging a surgical instrument.

6. The implant of claim 4, wherein the superior and inferior bone contacting members include interconnecting projections and bores.

7. The implant of claim 1, wherein the first and second bone contacting members and the at least one expandable wire netting are constructed as an integral part via a layer-wise manufacturing process.

8. The implant of claim 7, wherein the layer-wise manufacturing process is a selective laser melting process.

9. The implant of claim 7, wherein the layer-wise manufacturing process is a selective laser sintering process.

10. The implant of claim 1, wherein the at least one expandable wire netting is configured so that the first bone contacting member is separable from the second bone contacting member along the vertical direction.

11. The implant of claim 1, wherein the at least one wire netting is a first lateral wire netting, and wherein the first bone contacting member comprises at least two superior bone contacting components interconnected along the lateral direction via the first lateral wire netting.

12. The implant of claim 11, wherein the second bone contacting member comprises at least two inferior bone contacting components interconnected along the lateral direction via a second lateral wire netting, wherein each of the at least two inferior bone contacting components and the at least two superior bone contact components are independently moveable relative to each other.

13. The implant of claim 12, wherein the first lateral wire netting is configured so that the at least two superior bone contacting components can separate from each other along the lateral direction, and wherein the second lateral wire netting is configured so that the at least two inferior bone contacting components can separate from each other along the lateral direction.

14. An expandable implant device configured for insertion in an intervertebral space disposed between adjacent vertebral bodies, the expandable implant device comprising:
   superior vertebra contacting components;
   inferior vertebra contacting components spaced from the superior bone contacting component along a vertical direction;
   a first expandable wire netting that connects along the vertical direction the two superior components to the two inferior components; and
   a second expandable wire netting that connects along the lateral direction either 1) at least two of the superior components, or 2) at least two of the inferior components, wherein each of the superior and inferior vertebra contacting components are separately moveable relative to each other along the respective vertical direction and the lateral direction, wherein the expandable implant device is expandable from a first insertion configuration to a second expanded configuration.

15. An expandable implant device of claim 14, wherein the first expandable wire netting is configured such that the superior vertebra contacting components are separable from the inferior vertebra contacting components.

16. The expandable implant device of claim 15, wherein the second expandable wire netting is configured such that at least two superior vertebra contacting components or at least two inferior vertebra contacting components are separable along the lateral direction.

17. The expandable implant device of claim 15, wherein the second expandable wire netting connects the at least two superior vertebra contacting components, the device further comprising a third expandable wire netting that connects along the lateral direction the at least two of the inferior vertebra contacting components.

18. The expandable implant device of claim 15, wherein the first and second expandable wire nettings are configured to enable 1) each of the superior vertebra contacting components to separately conform to the superior vertebra when the expandable implant device is in the second expanded configuration, and 2) each of the inferior vertebra contacting components to separately conform to the inferior vertebra when the expandable implant device is in the second expanded configuration.

19. The expandable implant device of claim 14, wherein at least one the superior bone contacting components and at least one of the inferior bone contacting components can pivot relative to each other.

20. The expandable implant device of claim 14, wherein at least two of the superior bone contacting components can pivot relative to each other.

21. The expandable implant device of claim 14, wherein at least two of the inferior bone contacting components can pivot relative to each other.

22. The implant of claim 1, wherein the first and second bone contacting members are two superior components interconnected along the lateral direction.

23. The implant of claim 1, wherein the first and second bone contacting members are two inferior components interconnected along the lateral direction.

24. The implant of claim 1, wherein the first bone contacting members are two superior components interconnected along the lateral direction via a first lateral wire netting, wherein the second bone contacting member comprises two inferior components interconnected along the lateral direction via a second lateral wire netting, the first and second lateral wire nettings configured such that the two superior components and the two inferior bone components are independently separable along the lateral direction.

25. The implant of claim 1, wherein the first bone contacting member and the second bone contacting member can pivot relative to each other.

26. An expandable intervertebral implant defining a superior bone contacting surface, an inferior bone contacting surface spaced apart from the superior bone contacting surface along a vertical direction, the expandable intervertebral implant comprising:

a superior bone contacting member;
an inferior bone contacting member positioned relative to the superior contacting member along the vertical direction; and
at least one expandable wire netting that connects along the vertical direction the superior bone contact member to the inferior bone contacting member, the at least one expandable wire netting comprising a plurality of individual links arranged in at least a first row of links and a second rows of links moveably connected to the first row of links, the first row of links moveable along a vertical direction relative to the second row of links such that the bone contacting members are moveable relative to each other along at least the vertical direction to expand the implant from a first insertion configuration to a second expanded configuration.

27. The implant of claim 26, wherein the plurality the individual links are moveable in a vertical direction and at least a second direction that is angularly offset with the respect to the vertical direction.

28. The implant of claim 26, further comprising:
a cavity defined between the superior bone contacting member and the inferior bone contacting member; and
an expansion member insertable in the cavity, the expansion member capable of receiving a filling material so that injection of the filling material into the expansion member permits the wire netting interconnecting the superior and inferior bone contacting members to expand, thereby moving the superior bone contacting member with respect to the inferior bone contacting member such that the implant vertically expands from the first height to the second height.

29. The implant of claim 26, wherein the at least one expandable wire netting is a vertically expandable wire netting, and wherein the superior bone contacting member comprise at least two superior bone contacting components that are connected along a lateral direction that is perpendicular to the vertical direction by a first laterally expandable wire netting.

30. The implant of claim 29, wherein the inferior bone contacting member comprises at least two inferior bone contacting components that are connected along the lateral direction by a second laterally expandable wire netting.

31. The implant of claim 30, wherein the vertically expandable wire netting, and the first and second laterally expandable wire nettings are configured such that each of the at least two inferior bone contacting components and the at least two superior bone contact components are independently moveable relative to each other so as to conform to the vertebral bodies when the implant is disposed in the intervertebral space.

* * * * *